United States Patent
Kwiatkowski et al.

(10) Patent No.: US 6,730,790 B2
(45) Date of Patent: May 4, 2004

(54) CHLORINATED HETEROCYCLIC COMPOUNDS AND METHODS OF SYNTHESIS

(75) Inventors: Stefan Kwiatkowski, Lexington, KY (US); Miroslaw Golinski, Lexington, KY (US)

(73) Assignee: R.T. Alamo Ventures I. LLC, Beverly Hills, CA (US)

( * ) Notice: Subject to any disclaimer, the term of this patent is extended or adjusted under 35 U.S.C. 154(b) by 0 days.

(21) Appl. No.: 10/281,684

(22) Filed: Oct. 28, 2002

(65) Prior Publication Data

US 2003/0166677 A1 Sep. 4, 2003

Related U.S. Application Data

(60) Provisional application No. 60/360,954, filed on Mar. 1, 2002.

(51) Int. Cl.[7] ..................... A61K 31/47; C07D 215/16
(52) U.S. Cl. ........................ 546/155; 514/312
(58) Field of Search ............................ 546/155; 514/312

(56) References Cited

U.S. PATENT DOCUMENTS

| | | | | |
|---|---|---|---|---|
| 4,302,460 A | * | 11/1981 | Davies et al. ................ | 514/312 |
| 5,011,931 A | * | 4/1991 | MacLean et al. ............. | 546/155 |
| 5,079,164 A | * | 1/1992 | Kirkovits et al. ........ | 435/252.5 |
| 6,110,489 A | | 8/2000 | Cutler ......................... | 424/449 |
| 6,132,753 A | | 10/2000 | Cutler ......................... | 424/423 |
| 6,194,433 B1 | | 2/2001 | Cutler ......................... | 514/312 |
| 6,258,373 B1 | | 7/2001 | Cutler ......................... | 424/434 |
| 6,307,050 B1 | * | 10/2001 | Kwiatkowski et al. ....... | 546/155 |
| 6,451,813 B1 | | 9/2002 | Cutler et al. ................. | 514/312 |
| 6,458,804 B1 | * | 10/2002 | Cutler et al. ................. | 514/312 |

FOREIGN PATENT DOCUMENTS

| WO | 91/02724 | * 3/1991 |
|---|---|---|
| WO | WO 99/56666 | 11/1999 |

* cited by examiner

*Primary Examiner*—D. Margaret Seaman
(74) *Attorney, Agent, or Firm*—Medlen & Carroll, LLP

(57) ABSTRACT

Compositions of the present invention comprise chlorinated heterocyclic compounds, including racemic monochloroflosequinan, purified enantiomers of monochloroflosequinan and the sulfone derivative of monochloroflosequinan. The methods of the present invention comprise the synthesis of racemic monochloroflosequinan and derivatives thereof, including the sulfone derivative. Intermediates in the synthesis are also provided. The methods further comprise the synthesis of enantiomers of monochloroflosequinan.

26 Claims, 21 Drawing Sheets

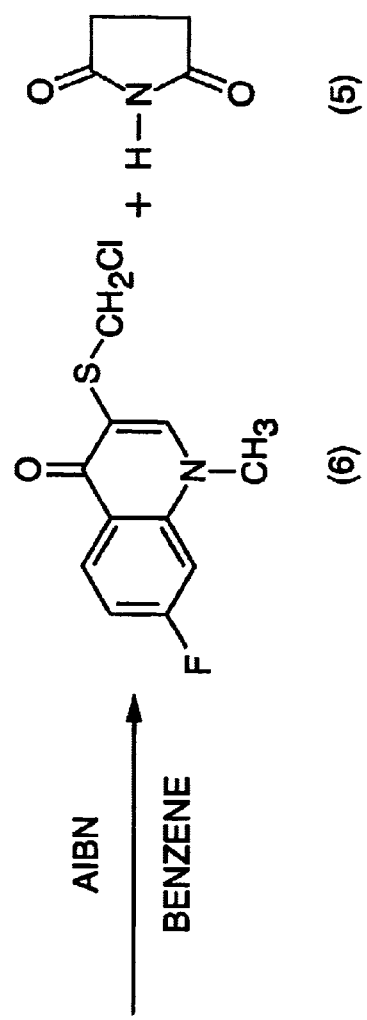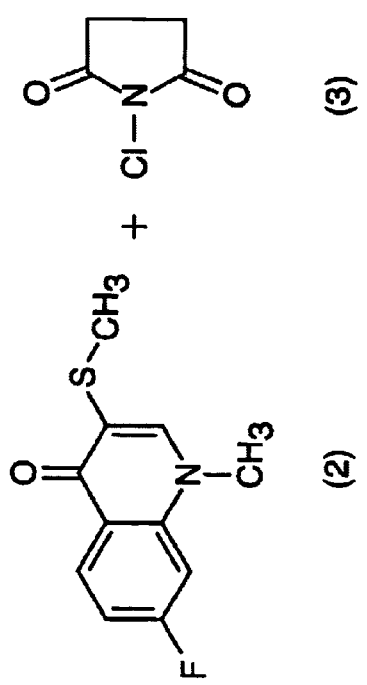
FIG. 9

| CAT. # | TARGET | BATCH* | SPP. | n= | CONC. | †% INHIBITION % -100 -50 0 50 100 | IC$_{50}$ | K$_I$ | n$_H$ | R |
|---|---|---|---|---|---|---|---|---|---|---|
| 146000 | PHOSPHODIESTERASE PDE1 | 41121 | BOV | 2 | 100 µM | 27 | | | | |
| 148000 | PHOSPHODIESTERASE PDE2 | 41120 | HUM | 2 | 100 µM | 29 | | | | |
| ◆ 152000 | PHOSPHODIESTERASE PDE3 | 41119 | HUM | 2 | 100 µM | 69 | 95.9 µM | | | |
| | | 41564 | HUM | 2 | 300 µM | 68 | | | | |
| | | | | 2 | 100 µM | 51 | | | | |
| | | | | 2 | 30 µM | 33 | | | | |
| | | | | 2 | 10 µM | 12 | | | | |
| | | | | 2 | 3 µM | 6 | | | | |
| | | | | 2 | 1 µM | -1 | | | | |
| 154000 | PHOSPHODIESTERASE PDE4 | 41118 | HUM | 2 | 100 µM | 17 | | | | |
| 156000 | PHOSPHODIESTERASE PDE5 | 41117 | HUM | 2 | 100 µM | 35 | | | | |
| 156100 | PHOSPHODIESTERASE PDE6 | 41116 | BOV | 2 | 100 µM | 17 | | | | |

*BATCH: REPRESENTS COMPOUNDS TESTED CONCURRENTLY IN THE SAME ASSAY(S).

◆ DENOTES ITEM MEETING CRITERIA FOR SIGNIFICANCE

†RESULTS WITH ≥ 50% STIMULATION OR INHIBITION ARE BOLDFACED (NEGATIVE VALUES CORRESPOND TO STIMULATION OF BINDING OR ENZYME ACTIVITY)

R=ADDITIONAL COMMENTS

BOV=BOVINE; HUM=HUMAN

FIG. 14

| CAT. # | TARGET | BATCH* | SPP. | n= | CONC. | †% INHIBITION -100 -50 0 50 100 | IC$_{50}$ K$_1$ n$_H$ R |
|---|---|---|---|---|---|---|---|
| ♦152000 | PHOSPHODIESTERASE PDE3 | 37072 | HUM | 2 | 100 μM | 67 | |
| ♦ | | 37527 | HUM | 2 | 300 μM | 73 | 28.2 μM |
| ♦ | | | | 2 | 100 μM | 65 | |
| ♦ | | | | 2 | 30 μM | 58 | |
| | | | | 2 | 10 μM | 42 | |
| | | | | 2 | 3 μM | 18 | |
| | | | | 2 | 1 μM | 1 | |
| 154000 | PHOSPHODIESTERASE PDE4 | 36817 | HUM | 2 | 100 μM | 15 | |
| 156000 | PHOSPHODIESTERASE PDE5 | 36818 | HUM | 2 | 100 μM | 37 | |
| 156100 | PHOSPHODIESTERASE PDE6 | 36819 | BOV | 2 | 100 μM | 16 | |

*BATCH: REPRESENTS COMPOUNDS TESTED CONCURRENTLY IN THE SAME ASSAY(S).

♦ DENOTES ITEM MEETING CRITERIA FOR SIGNIFICANCE

†RESULTS WITH ≥ 50% STIMULATION OR INHIBITION ARE BOLDFACED
(NEGATIVE VALUES CORRESPOND TO STIMULATION OF BINDING OR ENZYME ACTIVITY)

R=ADDITIONAL COMMENTS
BOV=BOVINE; HUM=HUMAN

FIG. 16B

CHLORINATED HETEROCYCLIC COMPOUNDS AND METHODS OF SYNTHESIS

This application claims benefit of provisional application No. 60/360,954 filed Mar. 1, 2002.

FIELD OF THE INVENTION

The present invention teaches the synthesis of chlorinated racemic heterocyclic compounds. Purified enantiomers of chlorinated heterocyclic compounds, and the synthesis of the same, are also taught in the present invention.

BACKGROUND

A variety of heterocyclic compounds have been described as having various pharmaceutical applications. However, the synthesis of such compounds, especially on a large scale, is often labor-intensive, expensive and time consuming. For compounds with a chiral center (i.e. compounds which have enantiomers), it is often desirable to be able to obtain a composition which is significantly enriched for one enantiomer over another enantiomer of the same compound, as enantiomers, while identical with respect to certain physical properties, such as melting and boiling points, may differ in their chemical, biological or biochemical properties.

In view of the different chemical, biological or biochemical properties associated with different enantiomers, chemists have explored many approaches for acquiring enantiomerically pure compounds including the resolution of the racemates using chiral stationary phases, structural modifications of naturally occurring chiral substances (as reagents for running stereospecific reactions) and asymmetric catalysis using chiral catalysts or enzymes.

Optically active catalysts or enzymes have limited application in multiple step and kilo scale processes due to their high prices. Similarly the use of chiral stationary phases, for optical resolution, is a very expensive means for kilo scale production.

What is needed, therefore, is a simplified and economical method for the stereospecific synthesis of heterocyclic compounds and acquisition of purified enantiomers for those compounds with chiral centers.

SUMMARY OF THE INVENTION

The present invention relates to heterocyclic compositions and methods for their synthesis. The compositions comprise a racemic mixture of monochloroflosequinan, and derivatives (e.g. the sulfone) thereof. Other compositions comprise enantiomers of monochloroflosequinan. The compositions also comprise chlorodesoxyflosequinan.

In one embodiment, the present invention contemplates compositions comprising racemic monochloroflosequinan (i.e. racemic 3-chloromethylsulfinyl-7-fluoro-1-methyl-4-quinolone). In another embodiment, the present invention contemplates compositions comprising the sulfone derivative of racemic monochloroflosequinan (i.e. 3-chloromethylsulfonyl-7-fluoro-1-methyl-4-quinolone). In one embodiment, the present invention contemplates compositions comprising a purified enantiomer of monochloroflosequinan, including derivatives thereof. In one embodiment, said purified enantiomer of monochloroflosequinan is a (+)-enantiomer (i.e. (S)-(+)-3-chloromethylsulfinyl-7-fluoro-1-methyl-4-quinolone). In another embodiment, said composition is substantially free of the (−)-enantiomer of monochloroflosequinan. In yet another embodiment, said purified enantiomer of monochloroflosequinan is a (−)-enantiomer (i.e. (R)-(−)-3-chloromethylsulfinyl-7-fluoro-1-methyl-4-quinolone). In another embodiment, said composition is substantially free of the (+)-enantiomer of monochloroflosequinan.

In some embodiments, a composition comprising a substantially purified enantiomer of monochloroflosequinan is contemplated. In some embodiments, the purified enantiomer (i.e. the (+)- or the (−)-enantiomer of monochloroflosequinan) represents at least 80% of the purified enantiomer preparation, more preferably at least 90%, more preferably at least 95% and even more preferably, at least 98% of the preparation. Likewise, the other enantiomer represents less than 20%, 10%, 5% or 2% of the preparation.

In some embodiments, a composition comprising an enantiomer of monochloroflosequinan (i.e. (S)-(+)-3-chloromethylsulfinyl-7-fluoro-1-methyl-4-quinolone or (R)-(−)-3-chloromethylsulfinyl-7-fluoro-1-methyl-4-quinolone) in enantiomeric excess is contemplated. In some embodiments, the major enantiomer in the composition is in at least 90% enantiomeric excess, and more preferably, 95% enantiomeric excess. In some embodiments, a composition comprising (S)-(+)-3-chloromethylsulfinyl-7-fluoro-1-methyl-4-quinolone having an optical purity of at least 85% is contemplated. In other embodiments, a composition comprising (S)-(+)-3-chloromethylsulfinyl-7-fluoro-1-methyl-4-quinolone having an optical purity of at least 95% is contemplated. In other embodiments, a composition comprising (R)-(−)-3-chloromethylsulfinyl-7-fluoro-1-methyl-4-quinolone having an optical purity of at least 85% is contemplated. In yet other embodiments, a composition comprising (R)-(−)-3-chloromethylsulfinyl-7-fluoro-1-methyl-4-quinolone having an optical purity of at least 95% is contemplated.

In one embodiment, the present invention contemplates compositions comprising chlorodesoxyflosequinan (i.e. 3-chloromethylthio-7-fluoro-1-methyl-4-quinolone).

In one embodiment, the present invention contemplates methods for the synthesis of racemic monochloroflosequinan. In another embodiment, the present invention contemplates methods for the synthesis of the sulfone derivative of racemic monochloroflosequinan. In yet other embodiments, the present invention contemplates methods for the stereopreferred synthesis (e.g. the preferential synthesis of one enantiomer) and separation of enantiomers of monochloroflosequinan. In one embodiment, a method for the synthesis of the (+)- enantiomer of monochloroflosequinan (i.e. (S)-(+)-3-chloromethylsulfinyl-7-fluoro-1-methyl-4-quinolone) in enantiomeric excess is contemplated. The method further provides additional separation steps. In another embodiment, a method for the synthesis of the (−)-enantiomer of monochloroflosequinan (i.e. (R)-(−)-3-chloromethylsulfinyl-7-fluoro-1-methyl-4-quinolone) in enantiomeric excess is contemplated. The method further provides additional separation steps. In some embodiments, the present invention provides methods of synthesis of chlorodesoxyflosequinan (i.e. 3-chloromethylthio-7-fluoro-1-methyl-4-quinolone).

In some embodiments, the present invention provides a method, comprising: a) providing: i) flosequinan, and ii) triphenyl phosphine; and b) reacting said flosequinan and triphenyl phosphine in an organic solvent under conditions such that desoxyflosequinan (7-fluoro-1-methyl-3-methylthio-4-quinolone) is produced; and c) further reacting said desoxyflosequinan with N-chlorosuccinimide and 2,2'-azobisisobutyronitrile in an organic solvent under conditions such that chlorodesoxyflosequinan (3-chloromethylthio-7-fluoro-1-methyl-4-quinolone) is produced. A variety of solvents can be used in this reaction. In some embodiments, said organic solvent in said reacting step b) is selected from the group consisting of carbon tetrachloride, xylene and toluene. In some embodiments, said providing step a) optionally provides iii) a catalyst, and said reacting step b) occurs in the presence of said catalyst. In some embodiments, said organic solvent in said reacting step b) is selected from the group consisting of xylene and toluene. A variety of solvents can be used in this reaction. A variety of catalysts are contemplated for this reaction. In some embodiments, said catalyst is tetrabromomethane. In some embodiments, said organic solvent in step c) is selected from the group consisting of carbon tetrachloride and benzene.

In another embodiment, the present invention provides a method, comprising:

a) providing: i) flosequinan, ii) thionyl chloride, and iii) pyridine; and b) reacting said flosequinan, thionyl chloride and pyridine in an organic solvent under conditions such that chlorodesoxyflosequinan (3-chloromethylthio-7-fluoro-1-methyl-4-quinolone) is produced.

In another embodiment, the present invention provides a method, comprising:

a) providing: i) chlorodesoxyflosequinan (3-chloromethylthio-7-fluoro-1-methyl-4-quinolone), ii) hydrogen peroxide, and iii) potassium carbonate; and b) reacting said chlorodesoxyflosequinan, hydrogen peroxide and potassium carbonate in a solvent under conditions such that monochloroflosequinan (3-chloromethylsulfinyl-7-fluoro-1-methyl-4-quinolone) is produced.

In yet other embodiments, the present invention provides a method, comprising:

a) providing: i) flosequinan, and ii) N-chlorosuccinimide; and b) reacting said flosequinan and N-chlorosuccinimide in an organic solvent under conditions such that monochloroflosequinan (3-chloromethylsulfinyl-7-fluoro-1-methyl-4-quinolone) is produced. A variety of solvents are contemplated. In some embodiments, said organic solvent is selected from the group consisting of carbon tetrachloride and benzene. In other embodiments, when said organic solvent is carbon tetrachloride, said reacting step b) additionally includes 2,2'-azobisisobutyronitrile.

In another embodiment, the present invention provides a method, comprising:

a) providing: i) chlorodesoxyflosequinan (3-chloromethylthio-7-fluoro-1-methyl-4-quinolone), and ii) a camphor based reagent; and b) reacting said chlorodesoxyflosequinan and camphor based reagent in an organic solvent under conditions such that an enantiomer of monochloroflosequinan is produced in enantiomeric excess. In some embodiments said camphor based reagent is (R)-(−)-(10-camphorsulfonyl) oxaziridine. In such embodiments, said enantiomer is (S)-(+)-3-chloromethylsulfinyl-7-fluoro-1-methyl-4-quinolone. In yet other embodiments, said camphor based reagent is (S)-(+)-(10-camphorsulfonyl) oxaziridine. In such embodiments, said enantiomer of monochloroflosequinan is (R)-(−)-3-chloromethylsulfinyl-7-fluoro-1-methyl-4-quinolone.

In some embodiments, a one-step method of synthesis of 3-chloromethylsulfinyl-7-fluoro-1-methyl-4-quinolone is contemplated. The method comprises: a) providing: i) flosequinan, and ii) N-chlorosuccinimide; and b) reacting, in an organic solvent, said flosequinan with said N-chlorosuccinimide under conditions such that 3-chloromethylsulfinyl-7-fluoro-1-methyl-4-quinolone is produced. A variety of solvents are contemplated. In some embodiments, said organic solvent is selected from the group consisting of carbon tetrachloride and benzene. In embodiments wherein the solvent is carbon tetrachloride, the reaction additionally includes 2,2'-azobisisobutyronitrile (AIBN).

In other embodiments, a three-step method of synthesis of 3-chloromethylsulfinyl-7-fluoro-1-methyl-4-quinolone is contemplated. The method comprises: a) providing: i) racemic flosequinan, and ii) triphenyl phosphine; and b) reacting said racemic flosequinan and said triphenylphosphine in an organic solvent under conditions such that 7-fluoro-1-methyl-3-methylthio-4-quinolone is produced; and c) further reacting said 7-fluoro-1-methyl-3-methylthio-4-quinolone with N-chlorosuccinimide and 2,2'-azobisisobutyronitrile in an organic solvent under conditions such that 3-chloromethylthio-7-fluoro-1-methyl-4-quinolone is produced; and d) reacting said 3-chloromethylthio-7-fluoro-1-methyl-4-quinolone with hydrogen peroxide under conditions such that 3-chloromethylsulfinyl-7-fluoro-1-methyl-4-quinolone is produced. A variety of solvents are contemplated. In some embodiments, the solvent in step b) is carbon tetrachloride. In some embodiments, the solvent in step c) is carbon tetrachloride. In some embodiments, potassium carbonate is included in said reacting step d).

In other embodiments, alternative methods for the synthesis of 3-chloromethylthio-7-fluoro-1-methyl-4-quinolone are contemplated. In one embodiment, the method comprises: a) providing: i) racemic flosequinan, ii) thionyl chloride, and iii) pyridine; and b) reacting said racemic flosequinan, thionyl chloride and pyridine under conditions such that 3-chloromethylthio-7-fluoro-1-methyl-4-quinolone is produced.

In yet other embodiments, methods for the synthesis of the sulfone derivative of monochloroflosequinan are contemplated. In one embodiment, the method comprises: a) providing: i) monochloroflosequinan (3-chloromethylsulfinyl-7-fluoro-1-methyl-4-quinolone), and ii) m-chloroperoxybenzoic acid; and b) reacting said monochloroflosequinan and said m-chloroperoxybenzoic acid under conditions such that monochloroflosequinan sulfone (3-chloromethylsulfonyl-7-fluoro-1-methyl-4-quinolone) is produced.

In other embodiments, 3-chloromethylthio-7-fluoro-1-methyl-4-quinolone is used in stereopreferred oxidation reactions to produce (S)-(+)-3-chloromethylsulfinyl-7-fluoro-1-methyl-4-quinolone or (R)-(−)-3-chloromethylsulfinyl-7-fluoro-1-methyl-4-quinolone. The mixture of enantiomers produced may then be subjected to further separation procedures. In one embodiment, the 3-chloromethylthio-7-fluoro-1-methyl-4-quinolone used in the subsequent synthesis and separation of enantiomers of monochloroflosequinan is synthesized by a method comprising: a) providing: i) racemic flosequinan, ii) triphenylphosphine, and iii) a catalyst; and b) reacting, in a solvent, said racemic flosequinan and said triphenylphosphine in the presence of said catalyst under conditions such that 7-fluoro-1-methyl-3-methylthio-4-quinolone is produced; and c) further reacting said 7-fluoro-1-methyl-3-methylthio-4-quinolone in a solvent with N-chlorosuccinimide and 2,2'-azobisisobutyronitrile under conditions such that 3-chloromethylthio-7-fluoro-1-methyl-4-quinolone is produced. Again, a variety of solvents are contemplated. In some embodiments, said solvent in step b) is toluene and said catalyst is tetrabromomethane ($CBr_4$).

In some embodiments, the method further provides the synthesis of (R)-(−)-3-chloromethylsulfinyl-7-fluoro-1-methyl-4-quinolone. The method further comprises d) reacting said 3-chloromethylthio-7-fluoro-1-methyl-4-quinolone with (S)-(+)-(10-camphorsulfonyl)oxaziridine under conditions such that (R)-(−)-3-chloromethylsulfinyl-7-fluoro-1-methyl-4-quinolone is produced in enantiomeric excess.

In other embodiments, the method further provides the synthesis of (S)-(+)-3-chloromethylsulfinyl-7-fluoro-1-methyl-4-quinolone. The method further comprises d) reacting said 3-chloromethylthio-7-fluoro-1-methyl-4-quinolone with (R)-(−)-(10-camphorsulfonyl)oxaziridine under conditions such that (S)-(+)-3-chloromethylsulfinyl-7-fluoro-1-methyl-4-quinolone is produced in enantiomeric excess.

In some embodiments, racemic flosequinan is reacted with triphenyl phosphine and a catalyst in anhydrous xylene to produce 7-fluoro-1-methyl-3-methylthio-4-quinolone. In some embodiments, the catalyst is tetrabromomethane ($CBr_4$). Thus, in one embodiment, a method of synthesis of 7-fluoro-1-methyl-3-methylthio-4-quinolone is provided, comprising: a) providing: i) racemic flosequinan, ii) anhydrous xylene, iii) a catalyst, and iv) triphenyl phosphine; and b) reacting said racemic flosequinan and said triphenyl phosphine in said anhydrous xylene in the presence of said catalyst under conditions such that 7-fluoro-1-methyl-3-methylthio-4-quinolone is produced. In one embodiment, said catalyst is tetrabromomethane ($CBr_4$).

DESCRIPTION OF THE DRAWINGS

FIG. 9 depicts the second step in the synthesis of e.e.(S)-(+)-3-chloromethylsulfinyl-7-fluoro-1-methyl-4-quinolone and (R)-(−)-3-chloromethylsulfinyl-7-fluoro-1-methyl-4-quinolone. In this step, 7-fluoro-1-methyl-3-methylthio-4-quinolone is chlorinated as described to produce 3-chloromethylthio-7-fluoro-1-methyl-4-quinolone.

FIG. 14 depicts the results of in vitro phosphodiesterase inhibition assays using monochloroflosequinan sulfone.

DEFINITIONS

Figure 1:
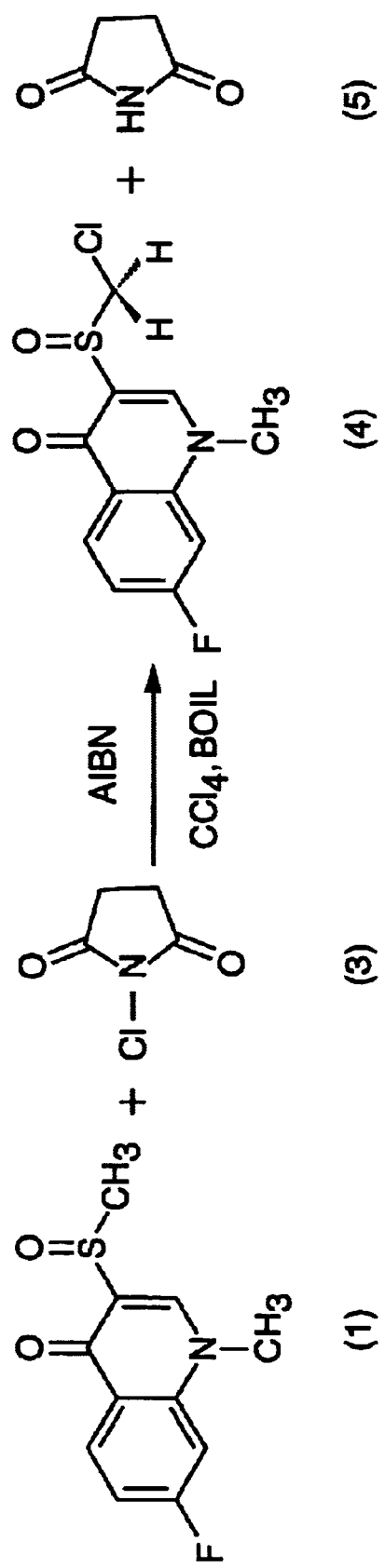
FIG. 1 depicts a one-step chemical synthesis of racemic monochloroflosequinan. Racemic flosequinan is chlorinated as described to produce monochloroflosequinan.

As used herein, "R and S" are used to denote the absolute configuration of the molecule about its chiral center(s).

As used herein, the prefixes "(+) and (−)" are employed to designate the sign of rotation of plane-polarized light by the compound, with (−) meaning that the compound is levorotatory (rotates to the left). A compound prefixed with (+) is dextrorotatory (rotates to the right).

As used herein, the terms "enantiomer" or "enantiomeric isomer" refer to stereoisomers of molecules that are non-superimposable mirror images of each other. Enantiomers have identical physical properties, such as melting points and boiling points, and also have identical spectroscopic properties. Enantiomers differ from each other with respect to their interaction with plane-polarized light and with respect to biological activity.

As used herein, the term "stereoisomer" refers to compounds that have their atoms connected in the same order but differ in the arrangement of their atoms in space. (e.g. L-alanine and D-alanine).

As used herein, the terms "racemic", "racemic mixture", or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

As used herein, the phrase "enantiomeric excess" or "e.e." refers to a reaction product wherein one enantiomer is produced in excess of the other and the percentage of the excess enantiomer is calculated using either (or both) of the following algorithms:

Algorithm No. 1: enantiomeric excess=(specific rotation of the reaction product/specific rotation of the pure enantiomer in excess)×100.

Algorithm No. 2: enantiomeric excess=[(moles of major enantiomer—moles of other enantiomer/total moles of both enantiomers)]×100.

As an example (the values in this example are offered for illustration only and do not represent data subsequently expressed in the "Experimental" section of this application), the observed rotation of a reaction product +8.52 degrees of rotation and the specific rotation of the R-configured enantiomer is reported as +15.00 degrees of rotation. The sign of the specific rotation of the reaction product indicates which enantiomer is in excess (e.g. in this example the R-configured isomer is in excess). If these values are inserted into Algorithm No. 1, the enantiomeric excess=(+8.52/+15.00)(100)=56.8% in excess of the R-isomer.

As used herein, the terms "purified enantiomer" and "purified enantiomer preparation" are meant to indicate a preparation (e.g. derived from non-optically active starting material, substrates or intermediates) wherein one enantiomer (for example, the (+) enantiomer) is enriched over the other, and more preferably, wherein the other enantiomer (for example the (−) enantiomer) represents less than 20%, more preferably less than 10% [e.g. in this particular instance, the (+) enantiomer is substantially free of the (−) enantiomer], and more preferably less than 5% and still more preferably, less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

Whether expressed as a "purified enantiomer" or "a compound in enantiomeric excess", the terms are meant to indicate that the amount of one enantiomer exceeds the amount of the other. Thus, when referring to an enantiomer preparation, both (or either of) the percent of the major enantiomer (e.g. by weight) and (or) the percent enantiomeric excess of the major enantiomer may be used to determine whether the preparation represents a purified enantiomer preparation.

As used herein, the term "optical purity" refers to the ratio of the observed optical rotation of a sample consisting of a mixture of enantiomers to the optical rotation of one pure enantiomer.

As used herein, the term "camphor based reagent" refers to a reagent (or reagents) comprising a camphor moiety, as shown below:

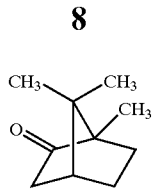

Camphor based reagents include, but are not limited to the following:

(R)-(−)-(10-camphorsulfonyl)oxaziridine:

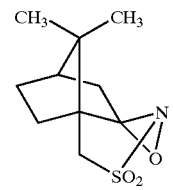

(S)-(+)-(10-camphorsulfonyl)oxaziridine:

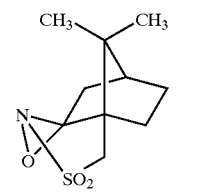

and (−)-(8,8-dichlorocamphorylsulfonyl)oxaziridine:

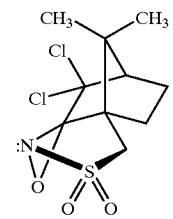

As used herein, the phrase "flosequinan" refers to 7-fluoro-1-methyl-3-(methylsulphinyl)-4(1H)-quinolinone which may also be described as 7-fluoro-1-methyl-3-(methylsulfinyl)-4(1H)-quinolone) and as 7-fluoro-1-methyl-3-methylsulfinyl-4-quinolone having the chemical structure of:

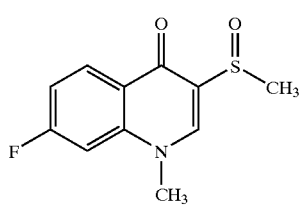

As used herein, the phrase "racemic flosequinan" or "flosequinan racemate" refers to a mixture of the two enantiomers of flosequinan. An ideal racemic mixture of the enantiomers of flosequinan refers to a 1:1 mixture of the S-(−)- and R-(+)-enantiomers of flosequinan, such that the optical rotation of the (+)-enantiomer cancels out the optical rotation of the (−)-enantiomer.

As used herein, "desoxyflosequinan" refers to 7-fluoro-1-methyl-3-methylthio-4-quinolone having the chemical structure of:

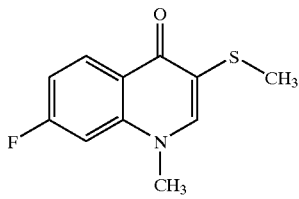

As used herein, "monochloroflosequinan" refers to the chemical composition designated as 3-chloromethylsulfinyl-7-fluoro-1-methyl-4-quinolone having the chemical structure corresponding to:

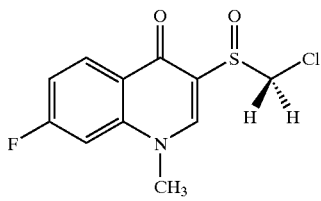

As used herein, the phrase "racemic monochloroflosequinan" or "monochloroflosequinan racemate" refers to a mixture of the two enantiomers of monochloroflosequinan. An ideal racemic mixture of the enantiomers of monochloroflosequinan refers to a 1:1 mixture of the (+)- and (−)-enantiomers of monochloroflosequinan, such that the optical rotation of the (+)-enantiomer cancels out the optical rotation of the (−)-enantiomer.

As used herein, "chlorodesoxyflosequinan" refers to the chemical composition designated as 3-chloromethylthio-7-fluoro-1-methyl-4-quinolone having the chemical structure corresponding to:

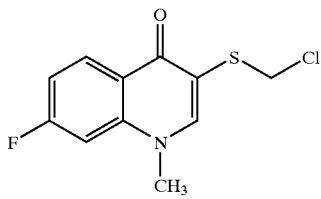

As used herein the "sulfone derivative of monochloroflosequinan" or "monochloroflosequinan sulfone" refers to the chemical composition designated as 3-chloromethylsulfonyl-7-fluoro-1-methyl-4-quinolone having the chemical structure corresponding to:

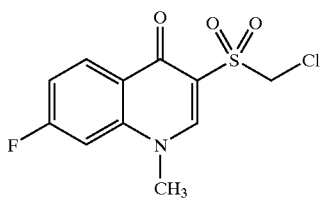

As used herein, the "(+)-enantiomer of monochloroflosequinan" or "(S)-(+)-monochloroflosequinan" refers to the chemical composition designated as (+)-3-chloromethylsulfinyl-7-fluoro-1-methyl-4-quinolone or (S)-(+)-3-chloromethylsulfinyl-7-fluoro-1-methyl-4-quinolone having the structure corresponding to:

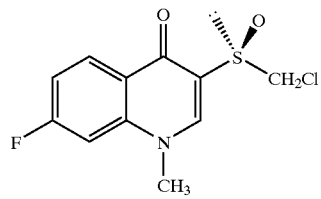

As used herein, the "(−)-enantiomer of monochloroflosequinan" or "(R)-(−)-monochloroflosequinan" refers to the chemical composition designated as (−)-3-chloromethylsulfinyl-7-fluoro-1-methyl-4-quinolone or (R)-(−)-3-chloromethylsulfinyl-7-fluoro-1-methyl-4-quinolone having the structure corresponding to:

As used herein, "room temperature", "RT" or "ambient temperature" is approximately 18° C. to 21° C.

As used herein, "overnight" is approximately 8 hours, more preferably 12 hours, more typically 17 hours, but can be up to approximately 30 hours.

As used herein, the term "heterocyclic compound" refers to a compound comprising a ring composed of atoms of more than one kind.

As used herein, "optical activity" refers to the property of certain substances to rotate plane polarized light. A compound or mixture of compounds which is "optically inactive" produces no net rotation of plane polarized light.

As used herein, a "catalyst" refers to a substance that, when added to a reaction mixture, changes (e.g. speeds up) the rate of attainment of equilibrium in the system without itself undergoing a permanent chemical change. Examples of suitable catalysts contemplated for use in the present invention include, but are not limited to, tetrabromomethane ($CBr_4$), carbon tetraiodide and iodide.

As used herein, an "organic solvent" refers to an organic substance that will dissolve other substances. Examples of organic solvents suitable for use in embodiments of the present invention include, but are not limited to carbon tetrachloride ($CCl_4$), xylene, toluene, benzene and methylene dichloride.

As used herein, the term "IBMX" corresponds to the structure having the chemical formula: 3-isobutyl-1-methylxanthine (available from Sigma).

DETAILED DESCRIPTION OF THE INVENTION

The present invention relates to heterocyclic compositions and methods for their synthesis. The methods of the present invention comprise the synthesis of heterocyclic compounds and the separation of enantiomers. In some embodiments, the compositions comprise a racemic mixture of monochloroflosequinan, including derivatives thereof. In a preferred embodiment, said monochloroflosequinan derivative is the sulfone derivative of monochloroflosequinan. In other embodiments, the compositions comprise a purified enantiomer of monochloroflosequinan, including derivatives thereof. In one embodiment, said purified enantiomer is the (+)-enantiomer of monochloroflosequinan (i.e. (S)-(+)-3-chloromethylsulfinyl-7-fluoro-1-methyl-4-quinolone). In one embodiment, said (+)-enantiomer of monochloroflosequinan is substantially free of the (−)-enantiomer of monochloroflosequinan. In other embodiments, said purified enantiomer is the (−)-enantiomer of monochloroflosequinan (i.e. (R)-(−)-3-chloromethylsulfinyl-7-fluoro-1-methyl-4-quinolone). In some embodiments, said (−)-enantiomer of monochloroflosequinan is substantially free of the (+)-enantiomer of monochloroflosequinan. It is not intended that the present invention be limited to complete separation of enantiomers, or 100% percent purity. It is sufficient that the preparation is enriched for one enantiomer (e.g. a 50:50 mixture becomes a 60:40 mixture).

Methods of producing a racemic mixture of flosequinan, as set out in U.S. Pat. Nos. 5,079,264 and 5,011,931 to MacLean et al., are hereby incorporated by reference. In one embodiment, racemic flosequinan is prepared according to the protocol set out in Example 8.

Without limiting the invention to any particular mechanism, racemic monochloroflosequinan, the enantiomers of monochloroflosequinan, and the sulfone derivatives of monochloroflosequinan are enzyme inhibitors. In specific examples, these compounds differentially inhibit various phosphodiesterases (e.g. PDE 1–6). The enzyme inhibition of racemic monochloroflosequinan, the enantiomers of monochloroflosequinan, and the sulfone derivatives of monochloroflosequinan has utility, for example, in therapeutics. Therefore, the present invention contemplates formulations an the administration of formulations to patients.

GENERAL DESCRIPTION OF CHEMICAL SYNTHETIC PROTOCOLS

In one embodiment, the synthesis of racemic monochloroflosequinan (3-chloromethylsulfinyl-7-fluoro-1-methyl-4-quinolone) may be carried out as a one step procedure, involving the direct chlorination of racemic flosequinan. In one embodiment, N-chlorosuccinimide is used in the chlorination. In one embodiment, the solvent is carbon tetrachloride (see Example 1), while in another embodiment the solvent is benzene (see Example 3).

In other embodiments, the synthesis of racemic monochloroflosequinan is carried out as a three step procedure, as described in more detail in Example 2. Briefly, in the first step, racemic flosequinan is reduced to desoxyflosequinan (7-fluoro-1-methyl-3-methylthio-4-quinolone). In the second step, desoxyflosequinan is chlorinated using N-chlorosuccinimide, to produce chlorodesoxyflosequinan (3-chloromethylthio-7-fluoro-1-methyl-4-quinolone). In the third step, chlorodesoxyflosequinan is subjected to oxidation to produce 3-chloromethylsulfinyl-7-fluoro-1-methyl-4-quinolone (monochloroflosequinan). Such oxidation may be accomplished using hydrogen peroxide.

In other embodiments, chlorodesoxyflosequinan is synthesized by reacting flosequinan with thionyl chloride and pyridine, as described in more detail in Example 4.

In yet other embodiments, the synthesis of monochloroflosequinan sulfone (3-chloromethylsulfonyl-7-fluoro-1-methyl-4-quinolone) is contemplated. In one embodiment, the synthesis of monochloroflosequinan sulfone is carried out by m-chloroperoxybenzoic acid oxidation of monochloroflosequinan, as described in Example 5.

In other embodiments, the synthesis and separation of enantiomers of monochloroflosequinan is contemplated. The (R)-(−)-enantiomer of monochloroflosequinan is synthesized by the stereopreferred oxidation of 3-chloromethylthio-7-fluoro-1-methyl-4-quinolone, followed by suitable separation procedures (see part C. of Example 6). The (S)-(+)-enantiomer of monochloroflosequinan is synthesized by the stereopreferred oxidation of 3-chloromethylthio-7-fluoro-1-methyl-4-quinolone, followed by suitable separation procedures (see part D. of Example 6).

The 3-chloromethylthio-7-fluoro-1-methyl-4-quinolone used as a substrate for the stereopreferred oxidation reactions may be synthesized by chlorination of 7-fluoro-1-methyl-3-methylthio-4-quinolone. In one embodiment, the chlorination is accomplished by the use of N-chlorosuccinimide (see part B. of Example 6). The 7-fluoro-1-methyl-3-methylthio-4-quinolone which serves as a substrate for the chlorination reaction may be produced by the catalytical reduction of 7-fluoro-1-methyl-3-methylsulfinyl-4-quinolone (see part A. of Example 6). A variety of catalysts are contemplated, including but not limited to tetrabromomethane, carbon tetraiodide and iodide. In one embodiment tetrabromomethane is used with toluene as the solvent (see part A. of Example 6). In another embodiment, anhydrous xylene is contemplated as the solvent, with tetrabromomethane as the catalyst (see Example 7).

The present invention also contemplates the formulation of comprising a racemic mixture of monochloroflosequinan, the enantiomers of monochloroflosequinan (and derivatives thereof) as a pharmaceutically acceptable salt. In addition, pharmaceutical formulations of a racemic mixture of monochloroflosequinan, the enantiomers of monochloroflosequinan (and derivatives thereof) may also contain binders, fillers, carriers, preservatives, stabilizing agents, emulsifiers, buffers and excipients as, for example, pharmaceutical grades of mannitol, lactose, starch, magnesium stearate, sodium saccharin, cellulose, and magnesium carbonate. The present invention also contemplates the administration of a racemic mixture of monochloroflosequinan, the enantiomers of monochloroflosequinan (and derivatives thereof) as a pharmaceutically acceptable salt or formulation. The present invention also contemplates the administration of a racemic mixture of monochloroflosequinan, the enantiomers of monochloroflosequinan (and derivatives thereof) formulations to a subject.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); L (liters); ml (milliliters); ° C. (degrees Centigrade).

All bracketed numbers [e.g. "(1)"] after the chemical name of a compound, refer to the corresponding chemical structure as designated by the same bracketed number in FIGS. 1 through 12.

All NMR spectra were recorded using Varian-Gemini 300 MHz Spectrometer.

In Examples 1–8, unless otherwise stated, the source for the chemical reagents was Aldrich, Milwaukee, Wis., USA (unless a reagent was synthesized do novo, as described in the examples). In Examples 1–7, Flosequinan was synthesized according to the protocol provided in Example 8, unless specified otherwise.

EXAMPLE 1

This example presents a one-step protocol for the synthesis of 3-chloromethylsulfinyl-7-fluoro-1-methyl-4-quinolone (racemic monochloroflosequinan) via the direct chlorination of 7-fluoro-1-methyl-3-methylsulfinyl-4-quinolone (racemic flosequinan) according to the synthetic scheme set out in FIG. 1. This overall synthesis is described in more detail according to the following reactions.

900 ml of anhydrous carbon tetrachloride and 25 g (0.015 mol) of 7-fluoro-1-methyl-3-methylsulfinyl-4-quinolone (1) (racemic flosequinan) were placed in a two L, round bottom reaction flask (equipped with a mechanical stirrer, a reflux condenser with gas outlet adapter, a thermometer and a gas inlet adapter in the fourth neck). The reaction flask was then immersed in an oil bath preheated to 95° C. while nitrogen gas was flowed over the reaction mixture (which was gently agitated) at a rate sufficient to prevent the infiltration of air into the reaction mixture. Once this reaction mixture reached a gentle boil, a mixture of N-chlorosuccinimide, compound (3), (15.5 g; 0.116 mole) and 1.1 g of 2,2'-azobisisobutyronitrile (AIBN) was added in five equal portions over 15 minute intervals. The mixture was boiled for an additional 30 minutes. The flask was then cooled to ambient temperature and the precipitated product was collected via filtration through a sintered glass filter. The precipitate was then washed with 50 ml of water, followed by 50 ml of acetone and finally recrystallized from 2.5 L of acetone, yielding 4.416 g of yellow crystals. Another 2.225 g of the product were collected when the first filtrate was concentrated to a volume of 750 ml. In total, 6.64 g (23.1% yield) of 3-chloromethylsulfinyl-7-fluoro-1-methyl-4-quinolone (4) (racemic monochloroflosequinan), of greater than 98% purity (as determined by NMR) were obtained. 1H NMR, $CDCl_3$; δ=3.95 s, 3H, N—$CH_3$; 4.92 dd, 2H, J=11.1 & 7.8 Hz, $CH_2$; 7.18–7.29 m, 2H, H at C6 and C8; 7.95 s, 1H, H at C2; 8.42–8.47 m, 1H, H at C5.

EXAMPLE 2

Figure 2:
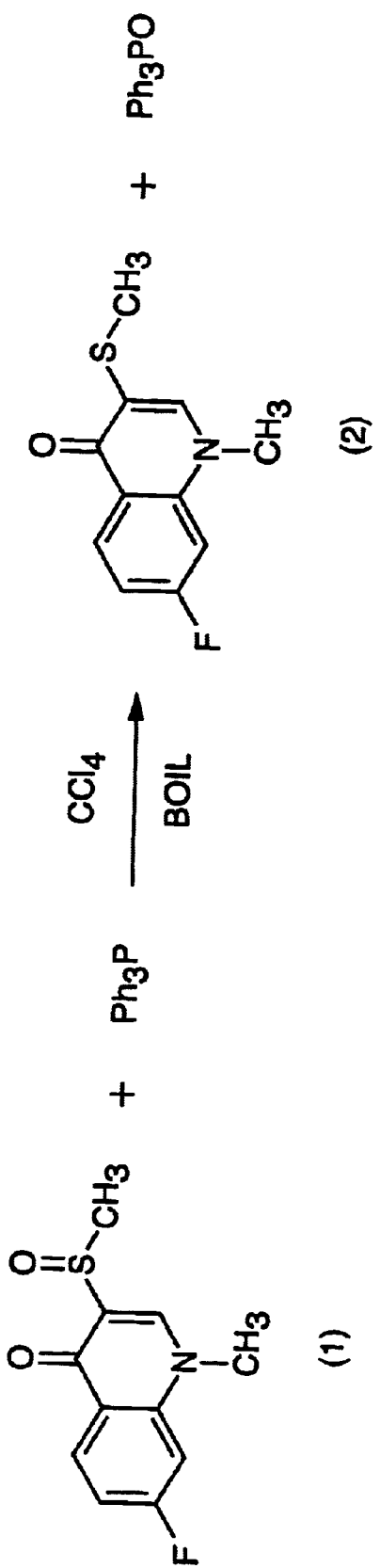
FIG. 2 depicts the first step in a three step protocol for the synthesis of racemic monochloroflosequinan. Triphenylphosphine reduction of flosequinan to 7-fluoro-1-methyl-3-methylthio-4-quinolone (desoxyflosequinan) is depicted.

This example presents an alternative three step protocol for the synthesis of 3-chloromethylsulfinyl-7-fluoro-1-methyl-4-quinolone (racemic monochloroflosequinan) according to the synthetic scheme set out in FIG. 2.

Step 1. Reduction of Flosequinan Racemate and Synthesis of 7-Fluoro-1-methyl-3-methylthio-4-quinolone (2) (Desoxyflosequinan)

The first step is triphenylphosphine reduction of the flosequinan to 7-fluoro-1-methyl-3-methylthio-4-quinolone (2) (desoxyflosequinan) as depicted schematically in FIG. 2. This reduction is accomplished according to the following protocol.

90 g (0.375 mole) of solid flosequinan racemate (1), 157.5 g (0.6 mole) of triphenyl phosphine ($Ph_3P$) and 3.5 L of carbon tetrachloride ($CCl_4$) were loaded into a 5 L, four neck round bottom flask, equipped with a mechanical stirrer, a thermometer, a reflux condenser with a nitrogen outlet at the top and an inlet for nitrogen. The reaction flask was then placed in an oil bath maintained at a temperature of 85–90° C.

Nitrogen gas then flowed over the reaction mixture at a rate sufficient to prevent the infiltration of air into the reaction mixture, and, thereby, substantially preventing oxidation of the product. The reaction mixture was then stirred and boiled for 2.5 hours. At this time, it was observed that all of the precipitates were dissolved and the color of the reaction mixture changed to an orange brown. The reaction mixture was then cooled to the ambient temperature overnight and the precipitated product was collected on a sintered glass filter. The precipitate was then washed in the filter with two 50 ml aliquots of cold carbon tetrachloride and dried under vacuum of approximately 2.00 mmHg. A 69.3 g of 7-fluoro-1-methyl-3-methylthio-4-quinolone (2) were collected. The approximate 3.5 L of carbon tetrachloride filtrate was concentrated to a final volume of 500 ml. As a result of this concentration an additional 3.3 g of the product (2) were collected. The total yield was 86.4% of 99+% clean (based on NMR spectra). 1H NMR, $CDCl_3$, δ=8.51 dd, 1H, J=6.6 & 9.0 Hz, H at C5; 7.83 s, 1H, H at C2; 7.14 m, 1H, H at C6; 7.05 dd, 1H, J=2.1 & 10.5 Hz, H at C8; 3.79 s, 3H, N—$CH_3$; 2.42 s, 3H, S—$CH_3$.

Step 2. Chlorination of Desoxyflosequinan With N-Chlorosuccinimide to Yield 3-chloromethylthio-7-fluoro-1-methyl-4-quinolone (6) (Chlorodesoxyflosequinan).

Figure 3:
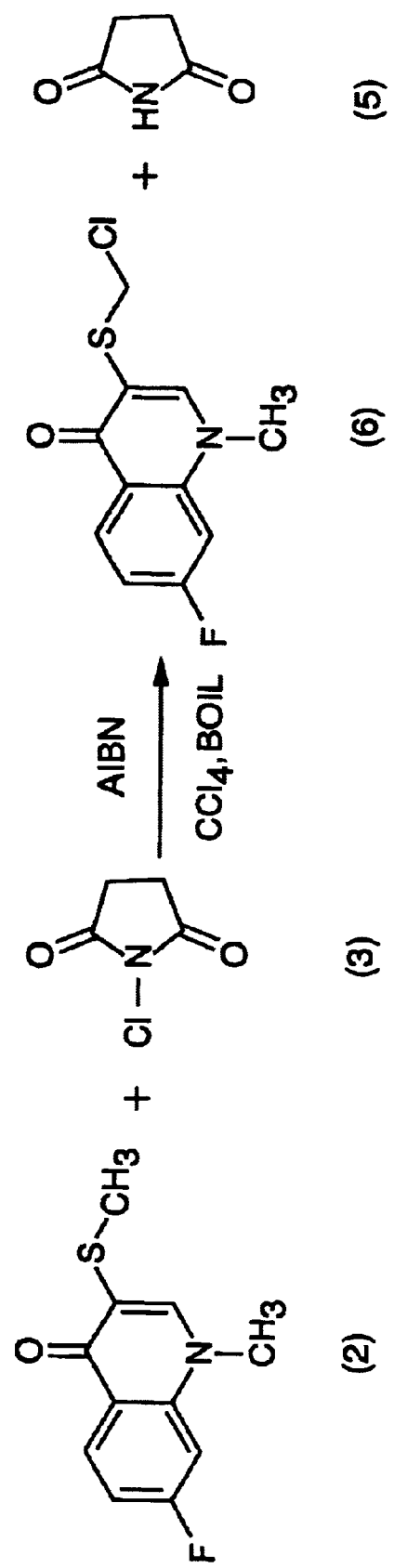
FIG. 3 depicts the second step in a three step protocol for the synthesis of racemic monochloroflosequinan. The chlorination of desoxyflosequinan with N-chlorosuccinimide to yield 3-chloromethylthio-7-fluoro-1-methyl-4-quinolone is depicted.

The reactions in the second step are depicted schematically in FIG. 3. This chlorination is accomplished according to the following protocol.

A solution of 450 mg (2.015 mmol) of 7-fluoro-1-methyl-3-methylthio-4-quinolone (2) (desoxyflosequinan) in 15 ml of carbon tetrachloride was brought to a boil in a round bottom flask. 280 mg (2.097 mmol) of N-chlorosuccinimide (3) with 50 mg of AIBN was added to the desoxyflosequinan and carbon tetrachloride and the resulting mixture was boiled for 6 hours. This solution was evaporated to dryness and the resulting precipitate was then dissolved in 25 ml of ethyl acetate. The solution was washed once with 10 ml of water and twice with 10 ml of brine and concentrated to dryness. The resulting solid was crystallized from 28 ml of acetone yielding 255 mg (49.1% yield) of white crystals of chlorodesoxyflosequinan (6). Chemical purity, based on 1H NMR, was 98+%. 1H NMR, $CDCl_3$, δ=8.50 dd, 1H, J=6.7 & 9.0 Hz, H at C5; 8.01 s, 1H, H at C2; 7.22–7.07 m, 2H, H at C6 and C8; 5.02 s, 2H, $CH_2$; 3.83 s, 3H, N—$CH_3$.

Step 3. Hydrogen Peroxide Oxidation of 3-Chloromethylthio-7-fluoro-1-methyl-4-quinolone (chlorodesoxyflosequinan) to 3-chloromethylsulfinyl-7-fluoro-1-methyl-4-quinolone (4) (Monochloroflosequinan).

Figure 4:
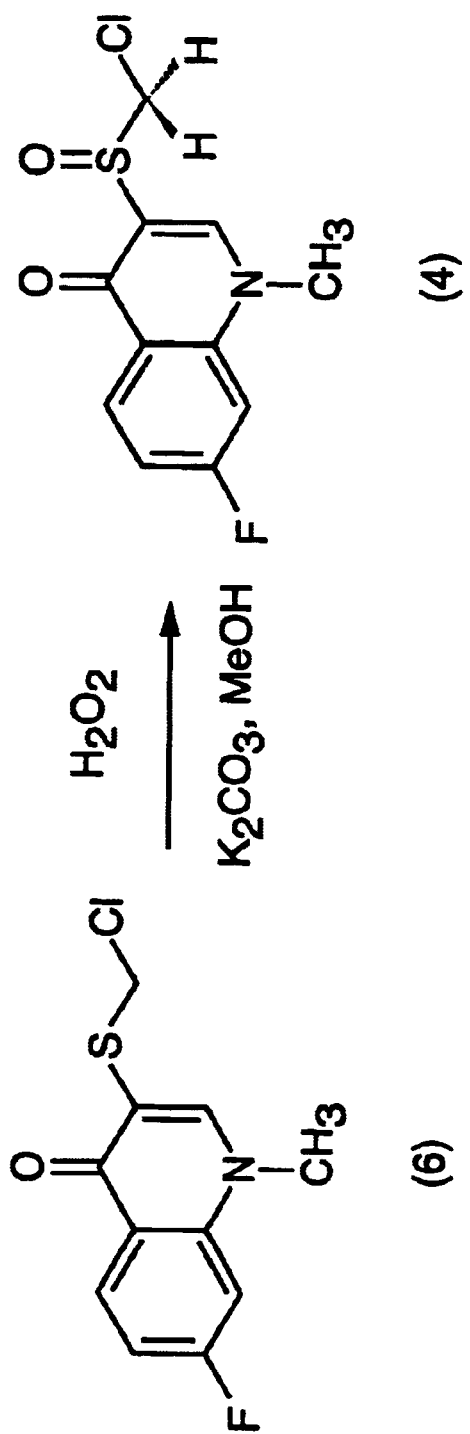
FIG. 4 depicts the third step in a three step protocol for the synthesis of racemic monochloroflosequinan. The hydrogen peroxide oxidation of chlorodesoxyflosequinan to monochloroflosequinan is depicted.

The reactions in the third step are depicted schematically in FIG. 4. This oxidation was accomplished according to the following protocol.

A solution of 250 mg (0.97 mmol) of chlorodesoxyflosequinan in 20 ml of methanol was stirred with 5 ml of 30% hydrogen peroxide and 1.2 g of solid potassium carbonate at ambient temperature overnight. The next day the organic layer was separated and evaporated to dryness yielding 255 mg, (96% yield) of the 97+% (by 1H NMR) clean monochloroflosequinan (4) with an NMR identical with the NMR for monochloroflosequinan synthesized in Example 1.

EXAMPLE 3

Figure 5:
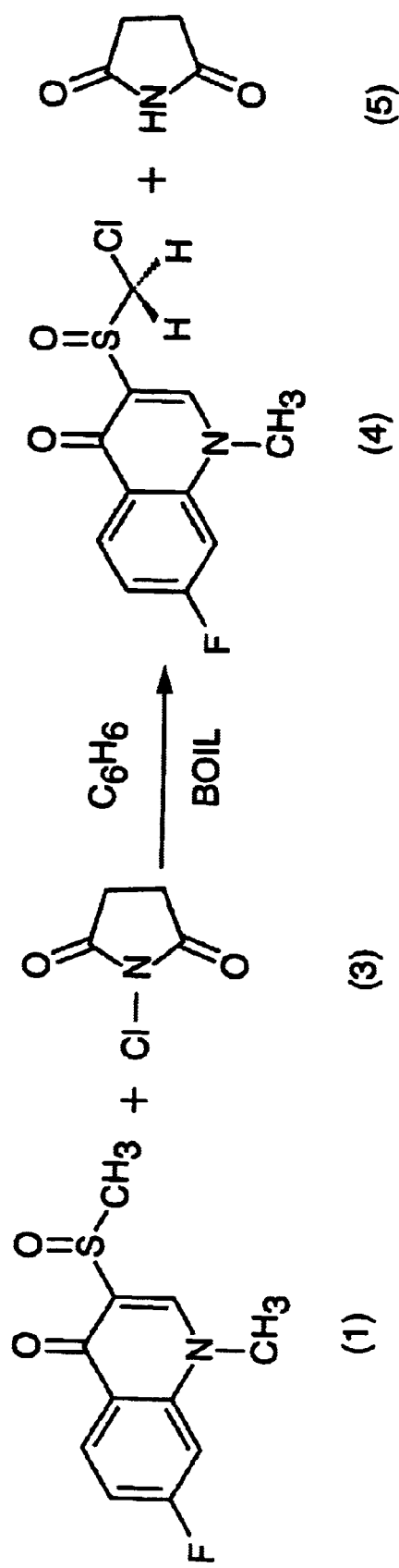
FIG. 5 depicts the synthesis of racemic monochloroflosequinan in an alternative solvent. Flosequinan is reacted as described to produce monochloroflosequinan.

This example presents an alternative solvent used in the synthesis of 3-chloromethylsulfinyl-7-fluoro-1-methyl-4-quinolone (4) (racemic monochloroflosequinan) according to the synthetic scheme set out in FIG. 5. This overall synthesis is described in more detail according to the following reactions.

A mixture of 2.39 g (0.01 mole) of flosequinan (1) and 1.67 g (0.0125 mole) of N-chlorosuccinimide (3) was suspended in 50 ml of anhydrous benzene and placed in a round bottom flask, then stirred and boiled under reflux for 15 minutes. The mixture was cooled to ambient temperature and crystals which precipitated were filtered off and crystallized from 35 ml of anhydrous ethanol, yielding after vacuum drying 2.58 g (94.3% yield) of 98+% clean (by 1H NMR) racemic monochloroflosequinan (4). 1H NMR, CDCl$_3$, δ=8.44 dd, 1H, J=6.0 & 8.7 Hz, H at C5; 7.95 s, 1H, H at C2; 7.29–7.22 m, 1H, H at C6; 7.20 dd, 1H, J=2.1 & 10.2 Hz, H at C8; 4.92 dd, 2H, J=11.1 & 27.0 Hz, CH$_2$; 3.95 s, 3H, N—CH$_3$.

EXAMPLE 4

Figure 6:
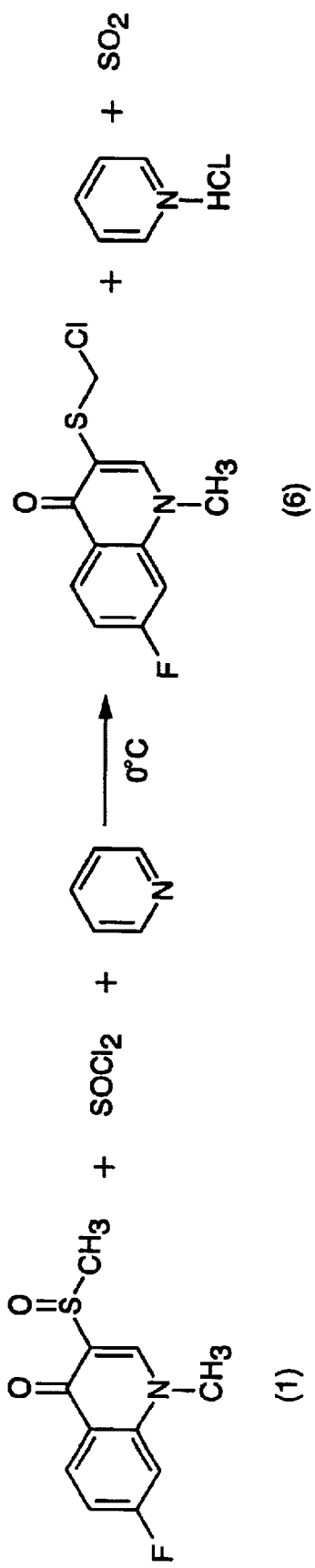
FIG. 6 depicts an alternative protocol for the synthesis of 3-chloromethylthio-7-fluoro-1-methyl-4-quinolone. Racemic flosequinan is reacted as described to produce 3-chloromethylthio-7-fluoro-1-methyl-4-quinolone.

This example presents an alternative protocol for the synthesis of 3-chloromethylthio-7-fluoro-1-methyl-4-quinolone (6) (chlorodesoxyflosequinan) according to the synthetic scheme set out in FIG. 6. This overall synthesis is described in more detail according to the following reactions.

3.59 g (5 mmole) of racemic flosequinan (1) were added (over the course of one minute) to a mixture of thionyl chloride (12 ml) and pyridine (3 ml) with efficient stirring and gentle cooling in a bath of dry ice and acetone, to keep the temperature in the range of 0° C. to 6° C. The mixture was stirred at approximately 0° C. for 5 minutes, cooled to −5° C. and poured as a thin stream into 350 ml of ice-water with efficient stirring. After 10 minutes of stirring at 0° C., a solid was filtered off, washed with water and dried over phosphorous pentoxide, under high vacuum producing 2.82 g (74% yield) of 95% pure (by 1H NMR) 3-chloromethylthio-7-fluoro-1-methyl-4-quinolone (6). 1H NMR, CDCl$_3$, δ=8.50 dd, 1H, J=6.6 & 9.0 Hz, H at C5; 8.01 s, 1H, H at C2; 7.18 ddd, 1H, J=2.1 & 9.0 & 10.2 Hz, H at C6; 7.09 dd, 1H, J=2.1 & 10.2 Hz, H at C8; 5.01 s, 2H, CH$_2$; 3.83 s, 3H, N—CH$_3$.

EXAMPLE 5

Figure 7:
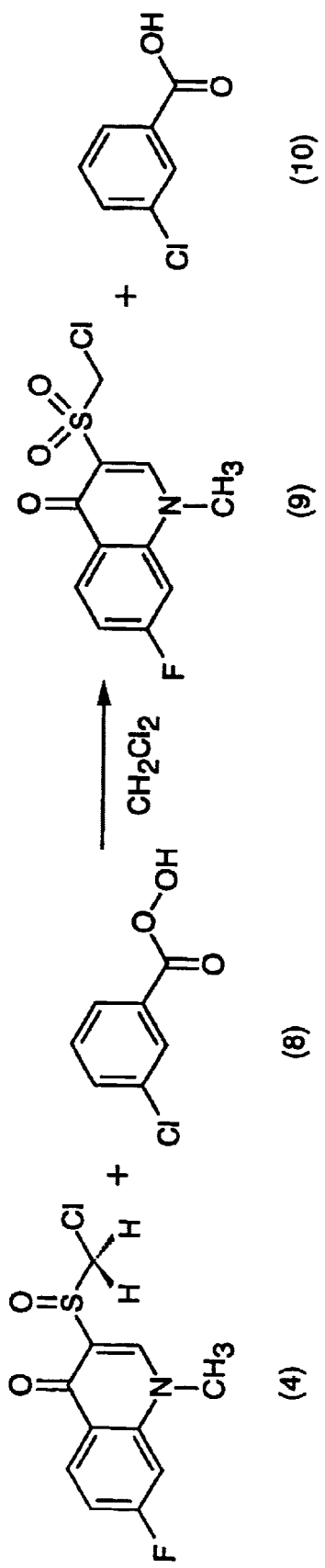
FIG. 7 depicts a protocol for the synthesis of monochloroflosequinan sulfone. Monochloroflosequinan is reacted as described to produce monochloroflosequinan sulfone.
Figure 8:
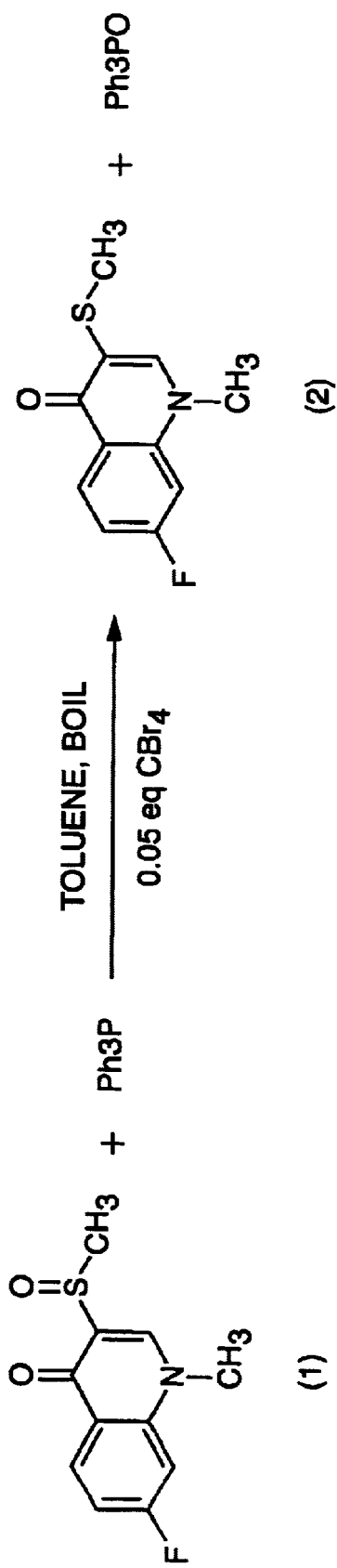
FIG. 8 depicts the first step in the synthesis of e.e. (S)-(+)-3-chloromethylsulfinyl-7-fluoro-1-methyl-4-quinolone and (R)-(−)-3-chloromethylsulfinyl-7-fluoro-1-methyl-4-quinolone. In this step, flosequinan is reacted as described to produce 7-fluoro-1-methyl-3-methylthio-4-quinolone.
Figure 10:
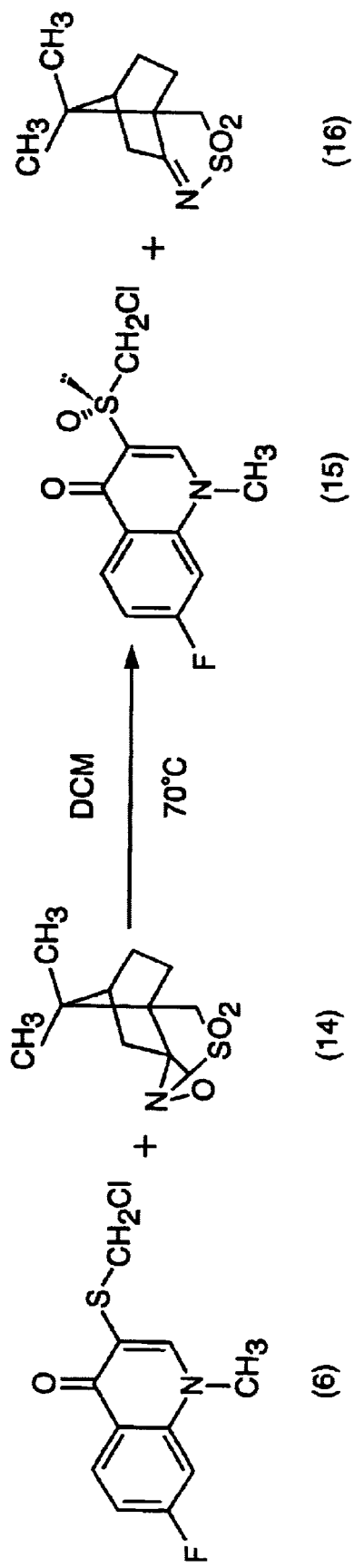
FIG. 10 depicts the stereopreferred oxidation of 3-chloromethylthio-7-fluoro-1-methyl-4-quinolone to produce (R)-(−)-3-chloromethylsulfinyl-7-fluoro-1-methyl-4-quinolone.
Figure 11:
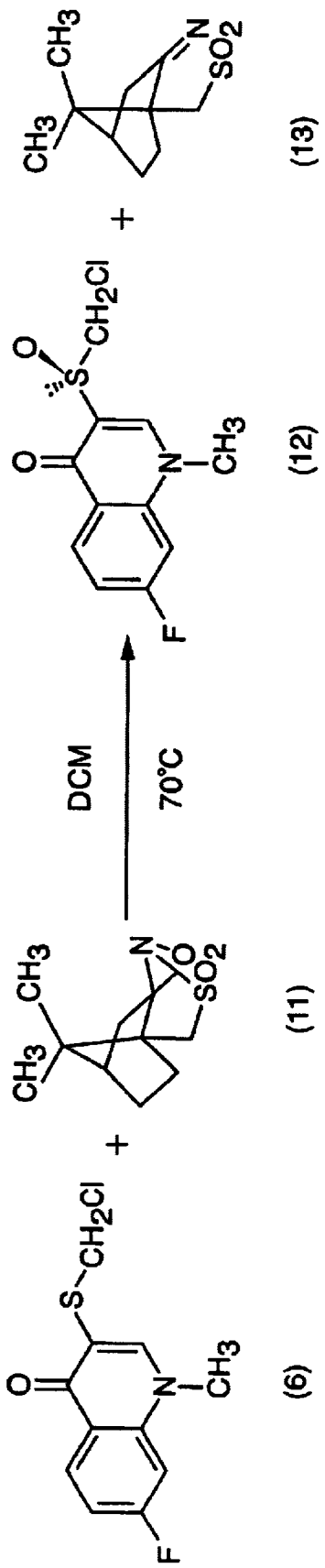
FIG. 11 depicts the stereopreferred oxidation of 3-chloromethylthio-7-fluoro-1-methyl-4-quinolone to produce (S)-(+)-3-chloromethylsulfinyl-7-fluoro-1-methyl-4-quinolone.

This example presents a protocol for the synthesis of 3-chloromethylsulfonyl-7-fluoro-1-methyl-4-quinolone (9) (monochloroflosequinan sulfone) according to the synthetic scheme set out in FIG. 7. This overall synthesis is described in more detail according to the following reactions.

6.33 g (0.0232 mole) of monochloroflosequinan (4) and 225 ml of methylene dichloride were placed in a 500 ml round bottom flask and stirred. Into this mixture a 5.98 g of 77% pure m-chloroperoxybenzoic acid (8) was added in four equal portions in 15 minute intervals and the mixture was stirred for an additional 30 minutes to complete oxidation. The reaction mixture was then concentrated to a final volume of 100 ml and the crystals which formed were filtered off and washed with two 10 ml portions of methylene dichloride. After high vacuum drying 5.2 g (77.6% yield) of white crystalline 3-chloromethylsulfonyl-7-fluoro-1-methyl-4-quinolone (9) were collected. The product was 99+% pure (by 1H NMR). 1H NMR, CDCl$_3$, δ=8.52 dd, 1H, J=6.3 & 9.0 Hz, H at C5; 8.41 s, 1H, H at C2; 7.20 dd, 1H, J=2.1 & 9.6 Hz, H at C8; 7.32–7.26 m, 1H, H at C6; 5.03 s, 2H, CH$_2$; 3.94 s, 3H, N—CH$_3$.

EXAMPLE 6

This example presents a protocol for the synthesis and separation of (S)-(+)-3-chloromethylsulfinyl-7-fluoro-1-methyl-4-quinolone and (R)-(−)-3-chloromethylsulfinyl-7-fluoro-1-methyl-4-quinolone.

A. Catalytical Reduction of 7-Fluoro-1-methyl-3-methylsulfinyl-4-quinolone Synthesis of 7-fluoro-1-methyl-3-methylthio-4-quinolone (Desoxyflosequinan). (see FIG. 8)

20.0 g (83.6 mmole) of 7-fluoro-1-methyl-3-methylsulfinyl-4-quinolone (1), 25.21 g (96.1 mmole, 1.15 equiv) of triphenylphosphine, 1.39 g (4.2 mmole, 0.05 equiv) of tetrabromomethane and 380 ml of toluene were placed in 500 ml flask equipped in a reflux condenser, and magnetic stirring rod. The mixture was refluxed for one hour and then placed in refrigerator for two hours (at −7° C.). The precipitate which formed was filtered off and washed two times with 25 ml of cold ethyl alcohol and finally vacuum dried yielding 14.75 g (82.7% yield) of 7-fluoro-1-methyl-3-methylthio-4-quinolone (2).

$^1$H NMR, CDCl$_3$, δ=8.512 dd, 1H, J=6.3 & 9.0, H at C5 7.82 s, 1H, H at C2 7.14 m, 1 H, H at C6 7.03 dd, $^1$H, J=2.4 & 10.5 Hz, H at C8 3.783 s, 3H, N—CH$_3$ 2.427 s, 3H, S—CH$_3$

B. NCS Chlorination of 7-Fluoro-1-methyl-3-methylthio-4-quinolone. Synthesis of 3-Chloromethylthio-7-fluoro-1-methyl-4-Quinolone (Chlorodesoxyflosequinan). (see FIG. 9)

12.67 g (56.76 mmol) of 7-fluoro-1-methyl-3-methylthio-4-quinolone (2) and 300 ml of benzene were added into a 500 ml round-bottomed flask and refluxed. Into this boiling solution, a mixture of 9.1 g (68.12 mmol, 1.2 equiv) N-chlorosuccinimide (NCS) (3) and 900 mg of 2,2$^1$-Azobisisobutyronitrile (AIBN) was added in three equal portions every five minutes. After 25 minutes of boiling, the mixture was extracted three times with 50 ml portions of water and the upper-organic layer was concentrated to dryness. The product was transferred on a filter with a total of 50 ml of ethylacetate and vacuum dried yielding 14.91 g (92.7% yield) of yellow crystals of 3-chloromethylthio-7-fluoro-1-methyl-4-quinolone (6).

$^1$HNMR, CDCl$_3$, δ=8.519 dd, J=6.3 & 9.0 Hz, H at C5 8.017 s, 1H, H at C2 7.215 m, $^1$H, H at C6 7.102 dd, 1H, J=2.7 & 10.5 Hz, H at C8 5.019 s, 2H, CH$_2$ 3.828 s, 3H, NCH$_3$

C. Stereopreferred Oxidation of 3-Chloromethylthio-7-fluoro-1-methy-4-quinolone Synthesis of (R)-(−)-3-chloromethylsulfinyl-7-fluoro-1-methyl-4-quinolone 7.0 g (27.16 n-mmol) of 3-chloromethylthio-7-fluoro-1-methyl-4-quinolone (6), 7.47 g (30.45 mmol, 1.12 equiv) of (S)-(+)-(10-camphor sulfonyl) oxaziridine (14) and 100 ml of dichloromethane were placed in a 250 ml pressure flask equipped with a magnetic stirring rod. The flask was tightly closed and placed in an oil bath of 70° C. for 72 hours. After this time the flask was cooled and examined for the presence of the substrates (see FIG. 10). Less than 15% of nonreacted chloromethylthio substrate and no oxaziridine were detected by $^1$H NMR spectroscopy. The dichloromethane solution was concentrated to dryness and crystallized from 100 ml of diethylketone: acetic acid/10:1 mixture to afford 4.36 g of clean (+)-(10-camphor sulfonyl)imine (16). The filtrate was concentrated again and the residue crystallized from 80 ml of anhydrous ethyl alcohol, yielding a mixture of 2.524 g, 37.2% e.e. of (R)-(−)-3-chloromethylsulfinyl-7-fluoro-1-methyl-4-quinolone (15) with 1.1 g of (+)-(10-camphorsulfonyl)imine (16).

The filtrate was concentrated to dryness yielding a mixture composed of: 3.2 g of 79% e.e. (R)-(−)-3-chloromethylsulfinyl-7-fluoro-1-methyl-4-quinolone, 0.88 g of unreacted 3-chloromethylthio-7-fluoro-1-methyl-4-quinolone, 0.7 g of unidentified by product and 2.1 g of (+)-(10-camphorsulfonyl)imine.

This mixture was chromatographed on silica gel column (55 cm+2 cm) using 0.5% methyl alcohol in dichloromethane as eluent. Fraction with $R_f$ value 0.4 were pooled together, concentrated to dryness and crystallized from 45 ml of diethylketone yielding 465 mg of 95.2% e.e. (R)-(−)-3-chloromethylsulfinyl-7-fluoro-1-methyl-4-quinolone. The ratio of (−) to (+) enantiomers was based upon HPLC analysis using:

Column: Chiracel OD-H (15 cm+4.6 mm, 5 μm particle size)
Eluent: methyl alcohol

This product specific rotation $[\alpha]_D^{20}=-460.0°$ was measured in $CHCl_3$ for 1 g/100 ml concentration.

$^1$H NMR, $CDCl_3$, δ=8.47 dd, 1H, J=6.3 & 8.7, H at C5 7.947 s, $^1$H, H at C2 7.264 m, $^1$H, H at C6 7.210 dd, 1H, J=2.7 & 10.5, H at C8 4.923 AB, 2H, J=12.0 & 28.2 Hz, $CH_2$ 3.947 s, 3H, $NCH_3$

The absolute configuration of the (−)-enantiomer of monochloroflosequinan was determined by X-ray crystallography.

D. Stereopreferred Oxidation of 3-Chloromethylthio-7-fluoro-1-methyl-4-quinolone Synthesis of (S)-(+)-3-chloromethylsulfinyl-7-fluoro-1-methyl-4-quinolone 7.0 g (27.16 mmol) of 3-chloromethylthio-7-fluoro-1-methyl-4-quinolone (6), 7.47 g (30.45 mmol, 1.12 equivalent) of (R)-(−)-(10-camphorsulfonyl) oxaziridine (11) and 200 ml of dichloromethane were placed in a 250 ml pressure flask equipped with a magnetic stirring rod. The flask was tightly closed and placed in an oil bath of 70° C. for 72 hours. After cooling to ambient temperature, the reaction mixture was concentrated to dryness and crystallized from 88 ml 1:10 mixture of ethylacetate and diethylketone. 1.2 g of 75% e.e. (S)-(+)-3-chloromethylsulfinyl-7-fluoro-1-methyl-4-quinolone (12) in a mixture with 2.5 g of (−)-(10-camphorsulfonyl)imine (13) were collected (see FIG. 11).

This mixture was separated using silica gel column (55 cm+2 cm). The imine was eluted first with 1% acetic acid in dichloromethane solution, while the product stayed absorbed on silica. Solution of (S)-(+)-3-chloromethylsulfinyl-7-fluoro-1-methyl-4-quinolone required 1:10 mixture of methyl alcohol and dichloromethane. Fractions containing (S)-(+)-3-chloromethylsulfinyl-7-fluoro-1-methyl-4-quinolone were pooled together yielding 770 mg of 87.5% e.e. material.

Final crystallization from 8 ml of ethyl acetate-diethylketone/1:10 mixture provided 503 mg of 96% e.e. (S)-(+)-3-chloromethylsulfinyl-7-fluoro-1-methyl-4-quinolone. The ratio of (+) to (−) enantiomers was based upon HPLC analysis using:

Column: Chiracel, OD-H (15 cm+4.6 mm, 5 μm particle size)
Eluent: methyl alcohol This product specific rotation $[\alpha]_D^{20}=+526°$ was measured in $CHCl_3$ for 1 g/100 ml concentration.

The absolute configuration of the (+)-enantiomer of monochloroflosequinan was determined by X-ray crystallography.

EXAMPLE 7

This example presents an alternative solvent for the catalytical reduction of flosequinan racemate (1) and synthesis of 7-fluoro-1-methyl-3-methylthio-4-quinolone (desoxyflosequinan) (2).

Figure 12:
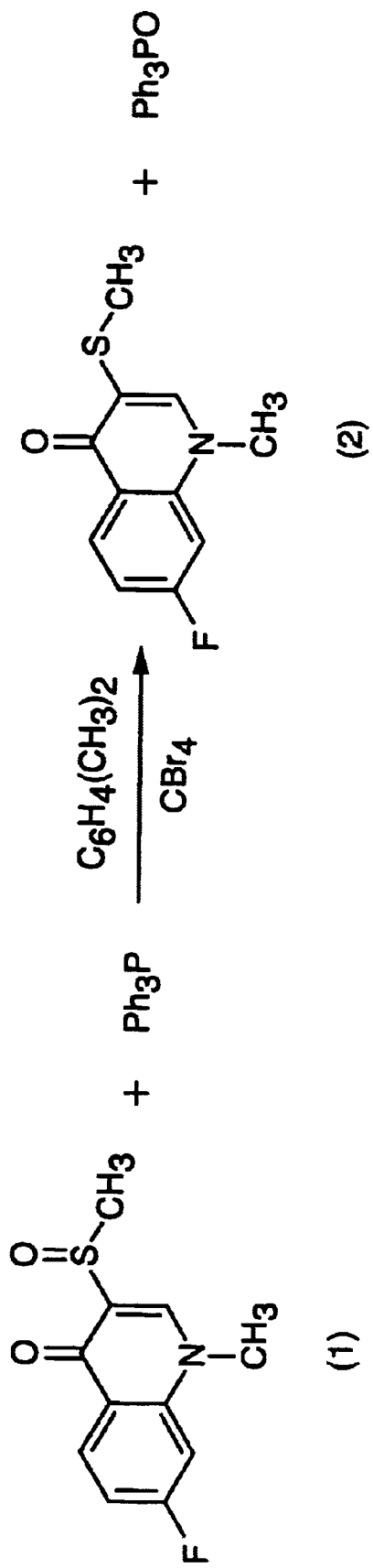
FIG. 12 depicts the use of an alternative solvent (anhydrous xylene) in the reduction of flosequinan to 7-fluoro-1-methyl-3-methylthio-4-quinolone (desoxyflosequinan).
Figure 13:
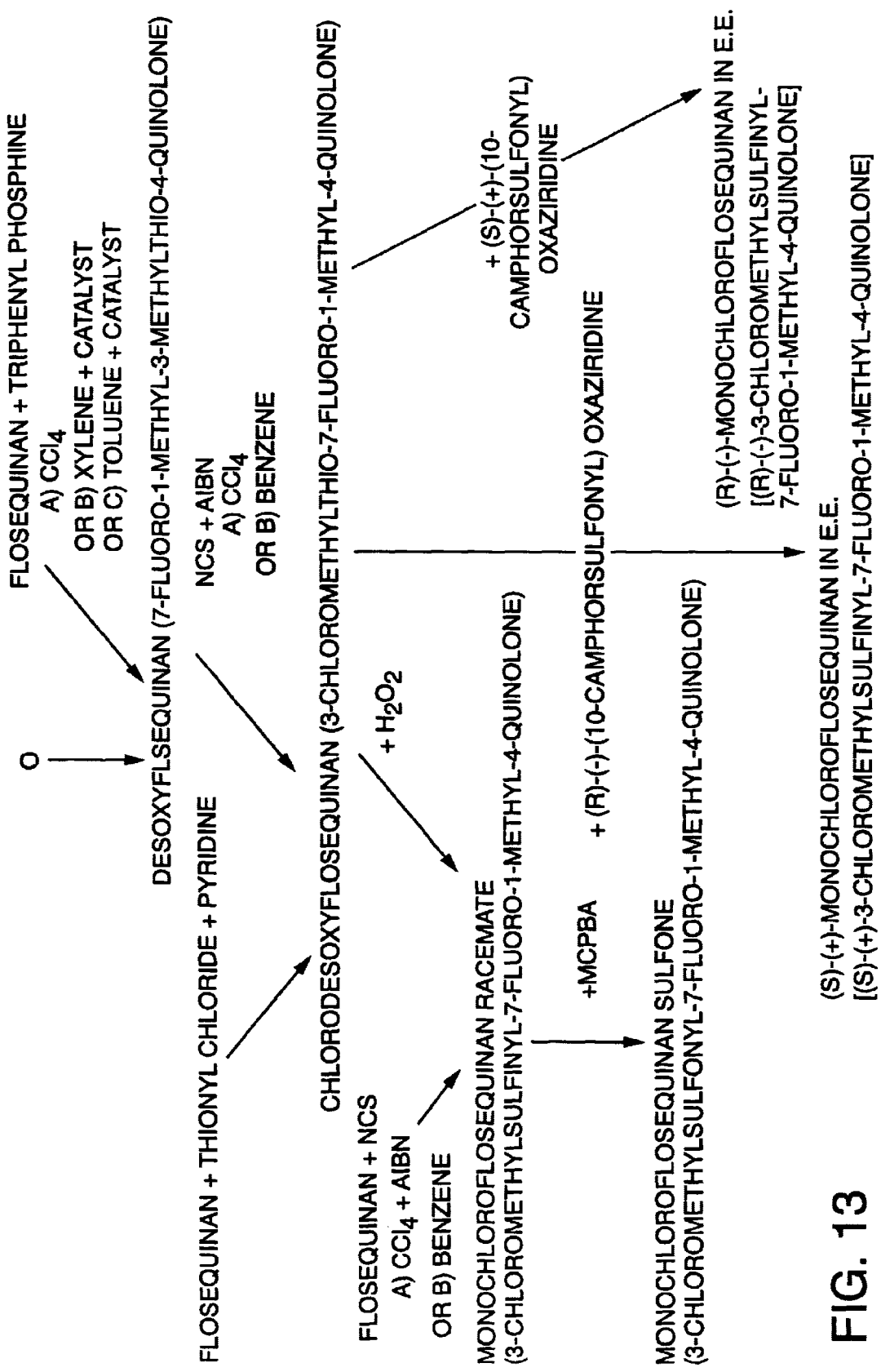
FIG. 13 outlines the various chemical reactions described in the description and examples.

FIG. 12 projects another scheme, using alternative solvents, for the reduction of flosequinan racemate (1) and synthesis of 7-fluoro-1-methyl-3-methylthio-4-quinolone (2). In this example, a 3.0 L round bottomed flask (with three necks) was equipped with a magnetic stirrer, a thermometer and an inlet of nitrogen. Into this flask was placed 2.0 L of anhydrous xylene [$C_6H_4(CH_3)_2$], 105 g (0.439 mole) of racemic flosequinan, 144 g (0.549 mole, 1.25 equivalent) of triphenylphosphine and 14.6 g (0.044 mole, 0.1 equivalent) of carbon tetrabromide ($CBr_4$). Nitrogen gas was then flowed over the reaction mixture at a rate sufficient to prevent the infiltration of air into the reaction mixture. The reaction mixture was stirred and heated to 100° C. for one hour. After this time the mixture was cooled to 10° C. and the product which precipitated was filtered off and washed with two 50 ml portions of xylene and subsequently dried under vacuum to yield 54.58 g of 98+% 7-fluoro-1-methyl-3-methylthio-4-quinolone (2).

The approximately 2.0 L of xylene filtrate was then concentrated (by evaporation) to the volume of 1.0 L, thereby, yielding additional 7-fluoro-1-methyl-3-methylthio-4-quinolone (2) crystals. These crystals were recrystallized from 150 g of ethanol to produce an additional 10.57 g of 98+% 7-fluoro-1-methyl-3-methylthio-4-quinolone, thereby, increasing the combined yield to a total of 65.15 g of 7-fluoro-1-methyl-3-methylthio-4-quinolone (2) which corresponded to a 66.4% yield.

1H NMR, CDC13, δ: 8.52 dd, 1H J=6.6&9,0 Hz, H-5; 7.89 s, 1H H-2; 7.15 ddd, 1 H, J=2.4 & 8.1 & 9.0 Hz, H-6; 7.08 dd, 1 H, J=2.1 & 10.2 Hz, H-8; 3.81 s, 3H, $NCH_3$; 2.43 s, 3H, $SCH_3$.

EXAMPLE 8

In this example racemic flosequinan is prepared according to the following protocol:

A. Preparation of Racemic Flosequinan
i. Step I

In a clean and dry 12 L glass reactor equipped with a back suction trap plus a NaOH (25%) trap at the outlet and a back suction trap in the inlet, 3.840 L of toluene were charged and cooled to −45° C. using a dry ice-acetone bath. Using appropriate safety precautions, 832 g of phosgene were then passed through the cold toluene while stirring to prepare a 20% (wt/wt) solution. The addition of the phosgene took approximately 3.5 hours.

Separately, into a clean and dry 22 L glass reactor equipped with the above-described types of back suction traps, 399 g of starting material (formula I):

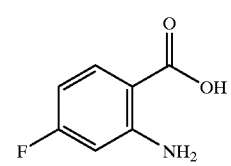

I was added with stirring to 4.37 L of deionized water. A separate 6.8% solution of sodium carbonate in water was also prepared by adding 297 g of sodium carbonate to 4.37 L of deionized water. Using a clean addition funnel, the sodium carbonate solution was then slowly added with stirring to the suspension of the starting material, to create a brown-colored solution.

In preparation for the reaction step, the phosgene solution was warmed from −45° C. to −15° C. and the mixture of the starting material and the sodium carbonate was cooled to 10° C. The phosgene solution was then added over approximately 1.5 hours with stirring to the brown solution. The reaction mixture was stirred overnight allowing the desired intermediate-A (formula II):

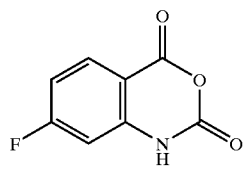

to precipitate out. A sample was removed for NMR assessment and the precipitate was filtered on a 4 L sintered glass funnel. The filtrate was washed with 2×500 ml aliquots of cold deionized water and dried under a vacuum at approximately 50° C. for 16 hours.

A 93.4% lot yield of 435 g of intermediate-A (formula II) was obtained. This procedure was repeated three more times, starting with approximately 400 g of starting material each time. Lot yields of 448 g (94.5%), 449 g (95.9%), and 459 g (96.8%) were obtained.

ii. Step II

In a 22 L oven dried glass reactor equipped with a reflex condenser, addition funnel and temperature recorder, 11.40 L of anhydrous tetrahydrofuran (THF) were added under nitrogen. To this reactor were also added 409 g of 60% sodium hydride in oil. Eight approximately equal portions of intermediate-A (formula II) were then added to the reactor, totaling 883 g altogether. As this reaction is exothermic, care was taken to avoid excessive heat and bubbling. Final temperature was 40° C., with a maximum observed temperature of 41° C. The reaction mixture was stirred until hydrogen gas evolution ceased.

To the reaction mixture was then slowly added 575 ml (766.4 g) of dimethyl sulfate, keeping the temperature below 50° C. Upon completion, the reaction mixture was stirred at 50° C. for 3 hours with the reflux condenser on. A sample was removed for NMR assessment, and the heat was turned off before stirring overnight.

In the morning, the stirring was stopped and the clear liquid on top was siphoned off. This liquid was filtered using a 2–3 inch thick Celite pad in a 2 L sintered glass funnel. The residue cake was kept covered to minimize contact with atmospheric moisture. The residue was collected and washed with 4 aliquots of anhydrous THF. The filtrate and the washings were evaporated to dryness using a rotary evaporator and the residue obtained was dried under vacuum at approximately 36–38° C. overnight. A sample was removed for NMR assessment of the amount of unreacted dimethyl sulfate present. The dried residue was then added to 1600 ml of a 1:3 toluene:hexane mixture and vigorously stirred. This mixture was then filtered and washed with 2×700 ml washings of 1:3 toluene:hexane mixture. A reference sample was removed for NMR assessment and the residue was dried at 51–50° C. under vacuum for 36 hours.

This batch yielded 871 g of intermediate-B (formula III):

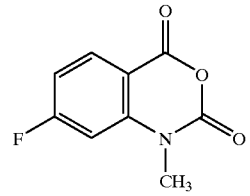

for a lot yield of 91.6%. Another 907.1 g of intermediate-A was subjected to the procedure of step II, in which the amounts of reactants and solvents was proportionately adjusted with a yield of 850 g (87%).

iii. Step III

In an oven dried 12 L glass reactor equipped with a stirrer, temperature recorder and addition funnel, 2550 ml of anhydrous toluene was added under nitrogen. Then 236 g of 60% sodium hydride in oil was added, all at room temperature. The reaction mixture was heated with continuous stirring to 75° C. using a heating mantel. Then 1.59 L of anhydrous dimethyl sulfoxide (DMSO) were added slowly and carefully over 45 minutes taking care to avoid excessive bubbling. The reaction mixture was stirred for one hour at 70–72° C. until clear and hydrogen gas evolution ceased. The heating mantel was turned off and a water bath was used to cool the reaction mixture to 30° C.

To this mixture, 538.2 g of dry intermediate-B (formula III) was added slowly in portions, keeping the temperature no higher than 35° C. Then 1.9 L of anhydrous DMSO was added, again keeping the temperature no higher than 35° C. The reaction mixture was stirred under nitrogen for one hour, allowing the mixture to cool to 26°. The reaction mixture was then quenched slowly and carefully with 320 ml of methanol. The resulting suspension was then added slowly and with vigorous stirring to a 22 L reaction vessel containing 12.760 L of diethyl ether.

After stirring was stopped, the upper ether layer was siphoned off and the brown oil lower layer was washed with 520 ml of fresh ether. The oily yellow residue was triturated with 2600 ml of deionized water until a yellow precipitate formed. This precipitate was filtered using a 2 L sintered glass funnel and the solid residue was washed with three aliquots of 130 ml cold deionized water. A reference sample was taken to assess the residue. The residue was dried under vacuum at 50–53° C. for 23 hours.

This procedure produced 243 g of intermediate C (formula IV):

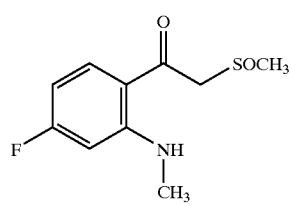

which represents a 38.4% yield. Two other batches of intermediate-B were treated according to this Step III procedure, with proportionate adjustments to the amounts of reactants and solvents. The first additional batch of 538.2 g intermediate-B produced a 192 g (30.4%) yield, and the second additional batch of 87.38 g of intermediate-B produced a yield of 42 g (40.9%).

iv. Step IV

In a 12 L oven dry glass reactor equipped with a stirrer, temperature recorder and addition funnel which has been dried by nitrogen flow for 30 minutes the following chemicals-were charged: 7.990 L of triethyl orthoformate; 696 g of intermediate-C; 324 ml of piperdine; and 296 ml of acetic acid. The reaction mixture was heated under nitrogen to reflux at approximately 105° C. for 2 hours. A sample was removed to assess the progress of the reaction step by NMR.

Using a water bath, the reaction mixture was then cooled to room temperature and stirred for 30 minutes. The final product precipitated out and was collected by filtration on a 4 L sintered glass funnel. The residue was washed with 3×700 ml aliquots of diethyl ether, and a sample was removed for NMR assessment. The residue was dried under vacuum at 50–51° C. for 17 hours. A sample of the dried flosequinan product (formula V):

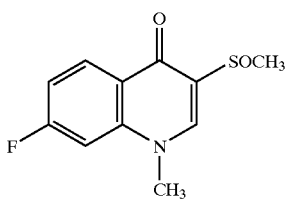

V was removed for NMR assessment. 547 g (75.3%) yield of flosequinan was obtained (an additional 47 g of product was scraped from the bottom of the sintered glass filter but was not included in this total yield calculation).

EXAMPLE 9

In this example, a racemic mixture of monochloroflosequinan and the sulfone derivative of monochloroflosequinan were independently subjected to biochemical enzyme assays to determine their respective percent inhibition of a variety of phosphodiesterases (PDE1–PDE6). The methods used have been adapted from those described in the scientific literature, see Hidaka and Asano "Human blood platelet 3':5' cyclic nucleotide phosphodiesterase. Isolation of low-Km and high Km phosphodiesterase." *Biochem. Biophys. Acta* 429:485 (1976); Nicholoson et at. "Differential modulation of tissue function and therapeutic potential of selective inhibitors of cyclic nucleotide phosphodiesterase isoenzymes" *Trends Pharmacol. Sci.* 12:19 (1991); Cortijo et al. "Investigation into the role of phosphodiesterase IV in bronchorelaxation, including studies with hyman bronchus." *Br. J. Pharmacol.* 108:562 (1993); Baehr et al. "Isolation and characterization of cGMP phosphodiesterase from bovine rod outer segments." *J. Biol. Chem.* 254:11669 (1979) and Gillespie and Beavo "Inhibition and stimulation of photoreceptor phosphodiesterase by dipyridamole and M&B 22,948" *Molecular Pharm.* 36:773 (1989). A brief summary of the conditions for each enzyme assay is provided below:

PDE1: PDE1 partially purified from bovine heart was used. The compounds were independently incubated with 13 $\mu$g PDE1 enzyme, 1.01 $\mu$M [$^3$H]cAMP+cAMP and CaCl$_2$/calmodulin in Tris buffer pH 7.5 for 20 minutes at either 25° C. or 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE2: PDE2 partially purified from human platelets was used. The compounds were independently incubated with 23 $\mu$g PDE2 enzyme, 25.1 $\mu$M [$^3$H]cAMP+cAMP in Tris buffer pH 7.5 for 20 minutes at either 25° C. or 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE3: PDE3 partially purified from human platelets was used. The compounds were independently incubated with 13 $\mu$g PDE3 enzyme and 1.01 $\mu$M [$^3$H]cAMP+cAMP in Tris buffer pH 7.5 for 20 minutes at either 25° C. or 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE4: PDE4 partially purified from human U-937 pronocytic cells was used. The compounds were independently incubated with 20 $\mu$g PDE4 enzyme and 1.01 $\mu$M [$^3$H] cAMP+cAMP in Tris buffer pH 7.5 for 20 minutes at either 25° C. or 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE5: PDE5 partially purified from human platelets was used. The compounds were independently incubated with 120 $\mu$g PDE5 enzyme and 1.01 $\mu$M [$^3$H]cGMP+cGMP in Tris buffer pH 7.5 for 20 minutes at either 25° C. or 30° C. The reaction was terminated by boiling for 2 minutes, and the resulting AMP was converted to guanosine by addition of 10 mg/ml snake venom nucleotidase and further incubation at 30° C. for 10 minutes. Unhydrolyzed cGMP was bound to AGI-X2 resin, and the remaining [$^3$H]guanosine in the aqueous phase was quantitated by scintillation counting.

PDE6: PDE6 partially purified from bovine retinal rod outer segments and activated by trypsin was used. The compounds were independently incubated with 0.2 $\mu$g/ml active PDE6 and 100 $\mu$M [$^3$H]cGMP+cGMP in Tris buffer pH 7.5 for 20 minutes at either 25° C. or 30° C. Each reaction was terminated by boiling for 2 minutes. The resulting GMP was converted to guanosine by addition of 10 mg/ml snake venom nucleotidase, and further incubated at 30° C. for 10 minutes. Unhydrolyzed cGMP was bound to AGI-X2 resin, and [$^3$H]guanosine remaining in the aqueous phase was quantitated by scintillation counting.

Figure 15:
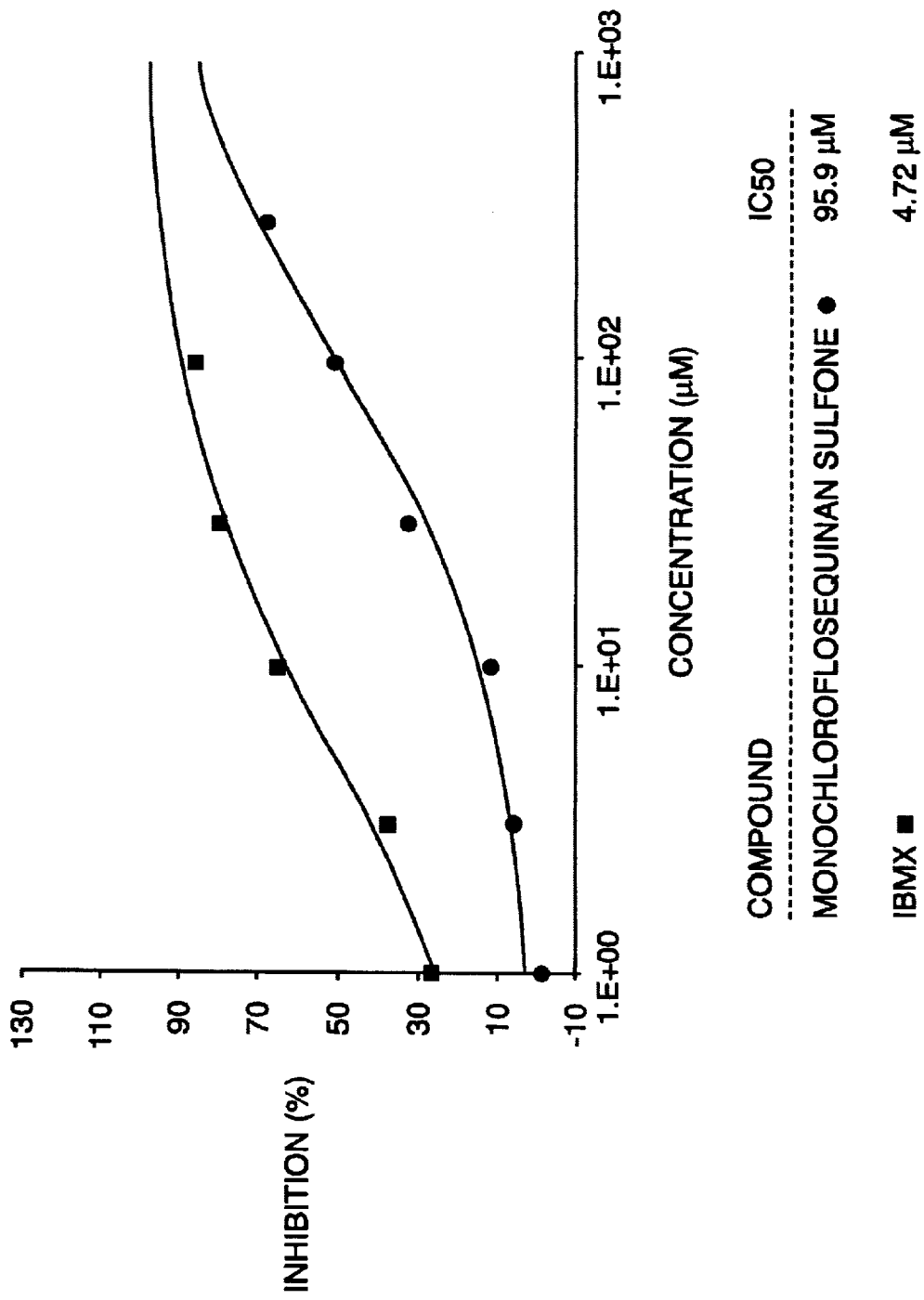
FIG. 15 shows the PDE3 inhibition curves for monochloroflosequinan sulfone (circles) and the reference compound, IBMX (squares).

FIG. 14 shows the results of assays carried out as described above with monochloroflosequinan sulfone. Each PDE was assayed at 25° C. with 100 $\mu$M monochloroflosequinan sulfone (in 1% DMSO as the vehicle). Significant inhibition (e.g. greater than 50% inhibition) of PDE3 was observed. PDE3 was also assayed with varying concentrations of monochloroflosequinan sulfone (300 $\mu$M, 100 $\mu$M, 30 $\mu$M, 10 $\mu$M, 3 $\mu$M and 1 $\mu$M) and the IC$_{50}$ was determined to be 95.9 $\mu$M (see FIGS. 14 and 15). FIG. 15 shows the inhibition curves for PDE3 for monochloroflosequinan sulfone (circles) and the reference compound, IBMX (squares).

Figure 16A:
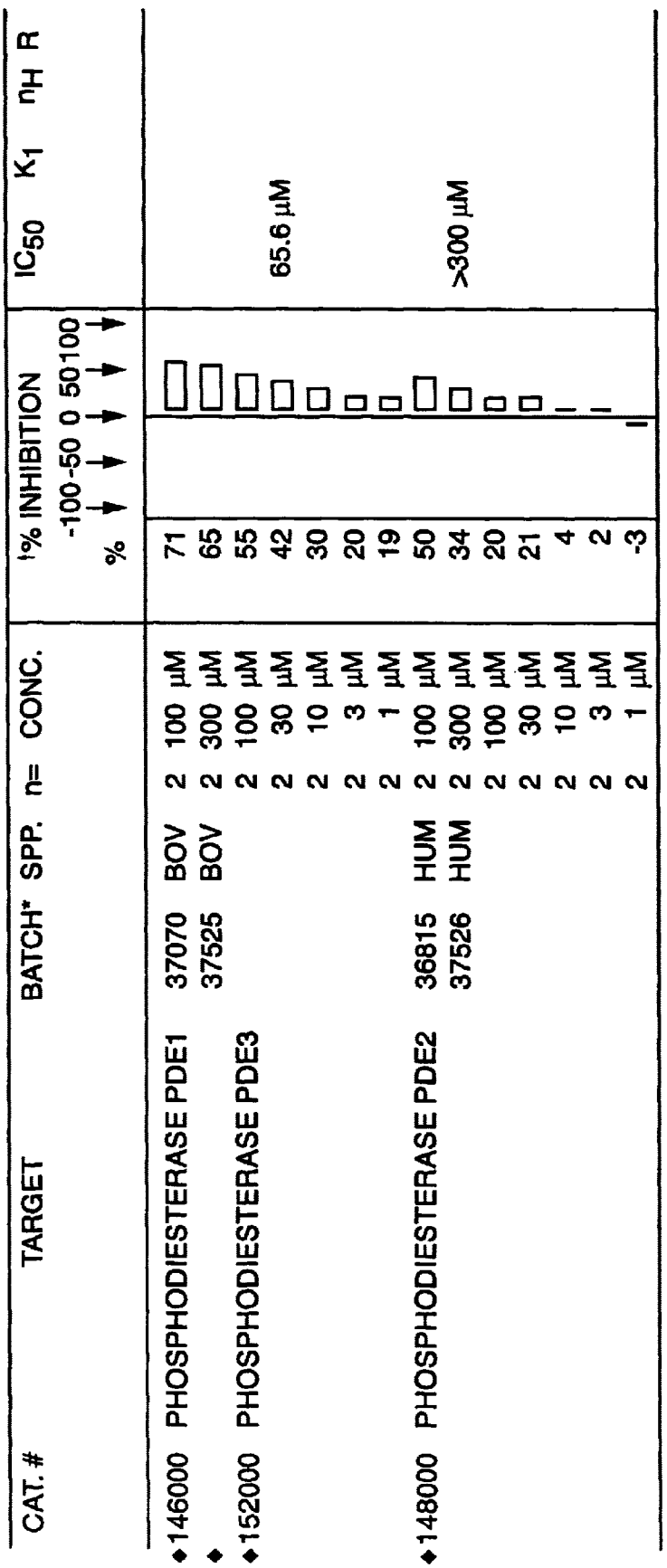
FIG. 16 depicts the results of in vitro phosphodiesterase inhibition assays using monochloroflosequinan.
Figure 17:
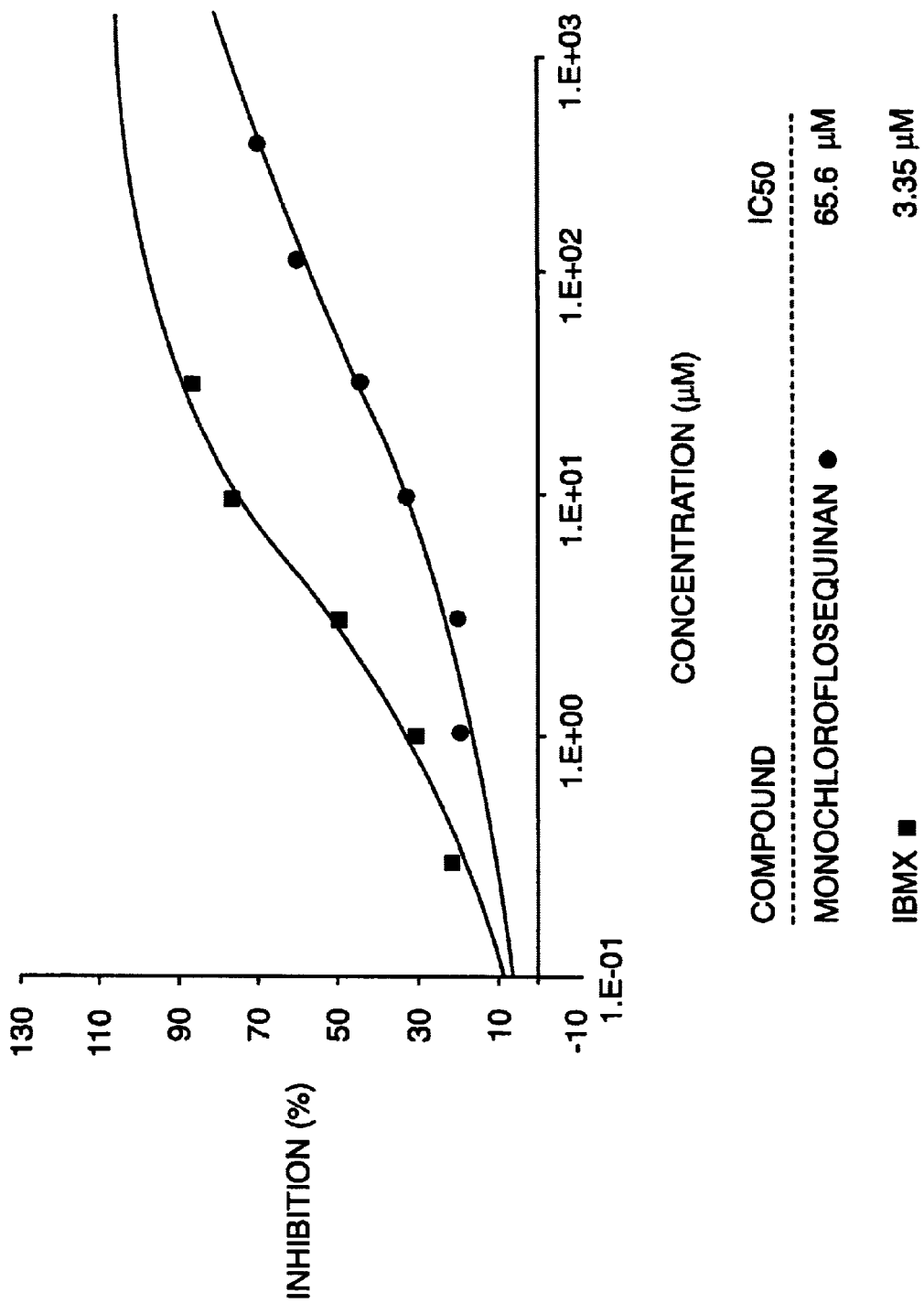
FIG. 17 shows the PDE1 inhibition curves for monochloroflosequinan (circles) and the reference compound, IBMX (squares).
Figure 18:
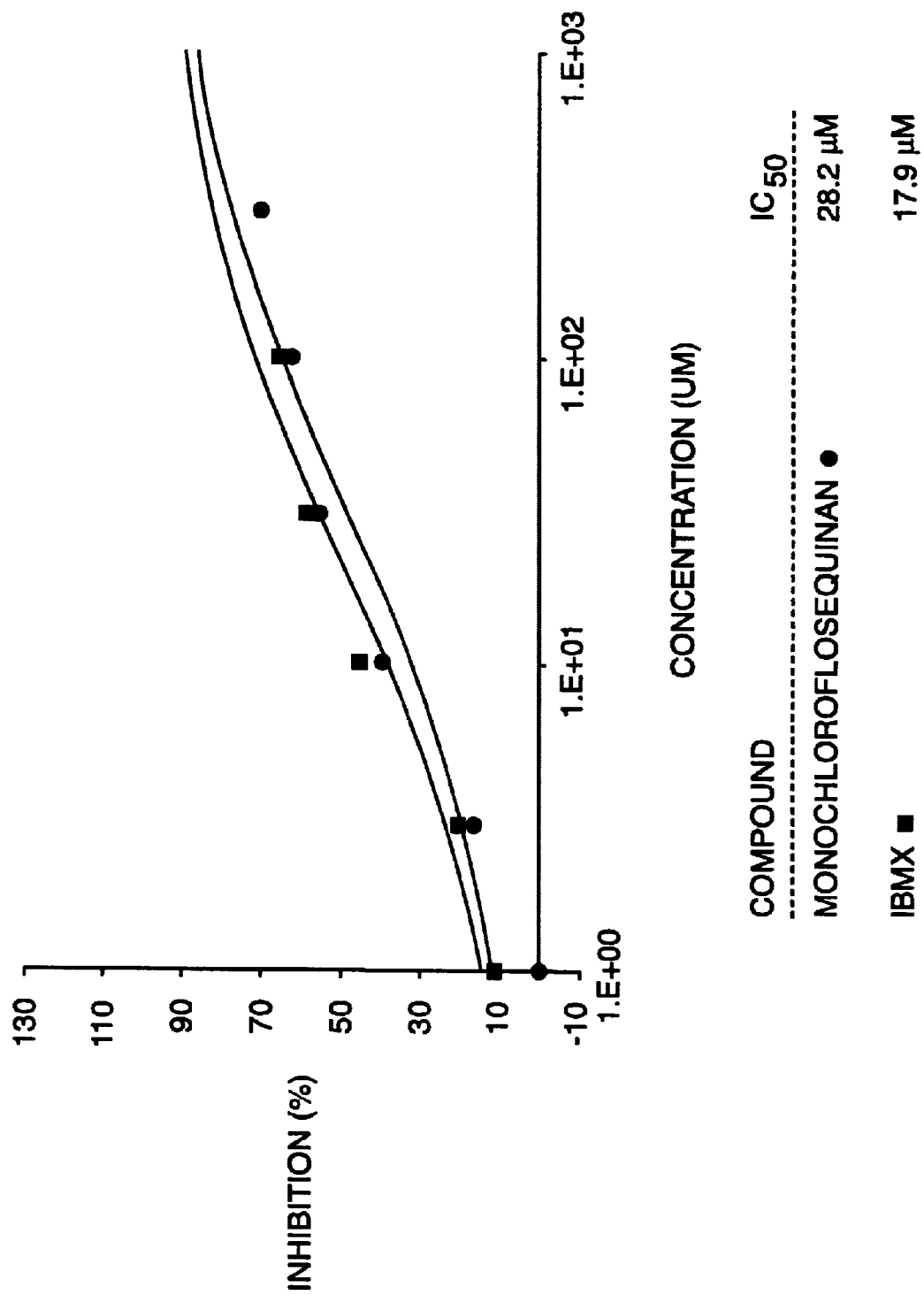
FIG. 18 shows the PDE3 inhibition curves for monochloroflosequinan (circles) and the reference compound, IBMX (squares).

FIG. 16 shows the results of assays carried out as described above with monochloroflosequinan. Each PDE was assayed at 30° C. with 100 $\mu$M monochloroflosequinan (in 1% DMSO as the vehicle). Significant inhibition of PDE1, PDE2 and PDE3 was observed in this assay. PDE1, PDE2 and PDE3 were also assayed with varying concentrations of monochloroflosequinan (300 µM, 100 µM, 30 µM, 10 µM, 3 µM and 1 µM) to determine the respective $IC_{50}$s. The $IC_{50}$ was determined to be 65.6 µM for PDE1, >300 µM for PDE2 and 28.2 µM for PDE3 (See FIGS. 16, 17 and 18). FIG. 17 shows the inhibition curves for PDE1 for monochloroflosequinan (circles) and the reference compound, IBMX (squares). FIG. 18 shows the inhibition curves for PDE3 for monochloroflosequinan (circles) and the reference compound, IBMX (squares).

Figure 19:
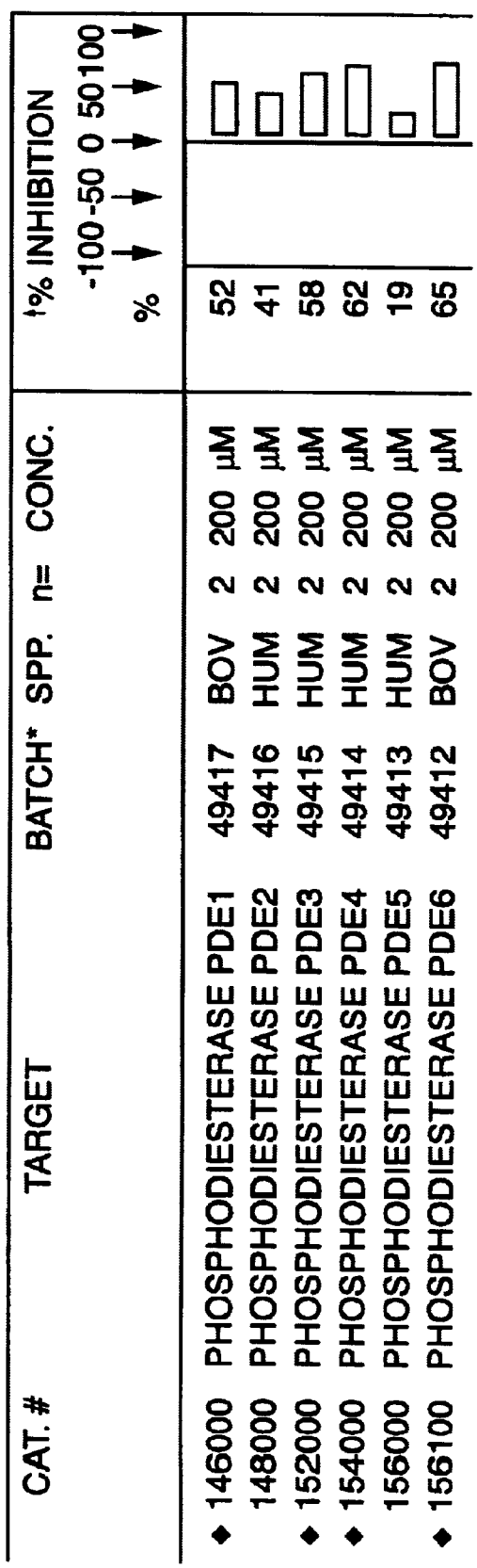
FIG. 19 depicts the results of in vitro phosphodiesterase inhibition assays using the (−)-enantiomer of monochloroflosequinan (i.e. (R)-(−)-3-chloromethylsulfinyl-7-fluoro-1-methyl-4-quinolone).

FIG. 19 shows the results of assays carried out as described above with the (−)-enantiomer of monochloroflosequinan (i.e. (R)-(−)-3-chloromethylsulfinyl-7-fluoro-1-methyl-4-quinolone). Each PDE was assayed at 25° C. with 200 µM of the (−)-enantiomer of monochloroflosequinan (i.e. (R)-(−)-3-chloromethylsulfinyl-7-fluoro-1-methyl-4-quinolone). (in 1% DMSO as the vehicle). Significant inhibition (e.g. greater than 50% inhibition) of PDE1, PDE3, PDE4, and PDE6 was observed in this assay.

Figure 20:
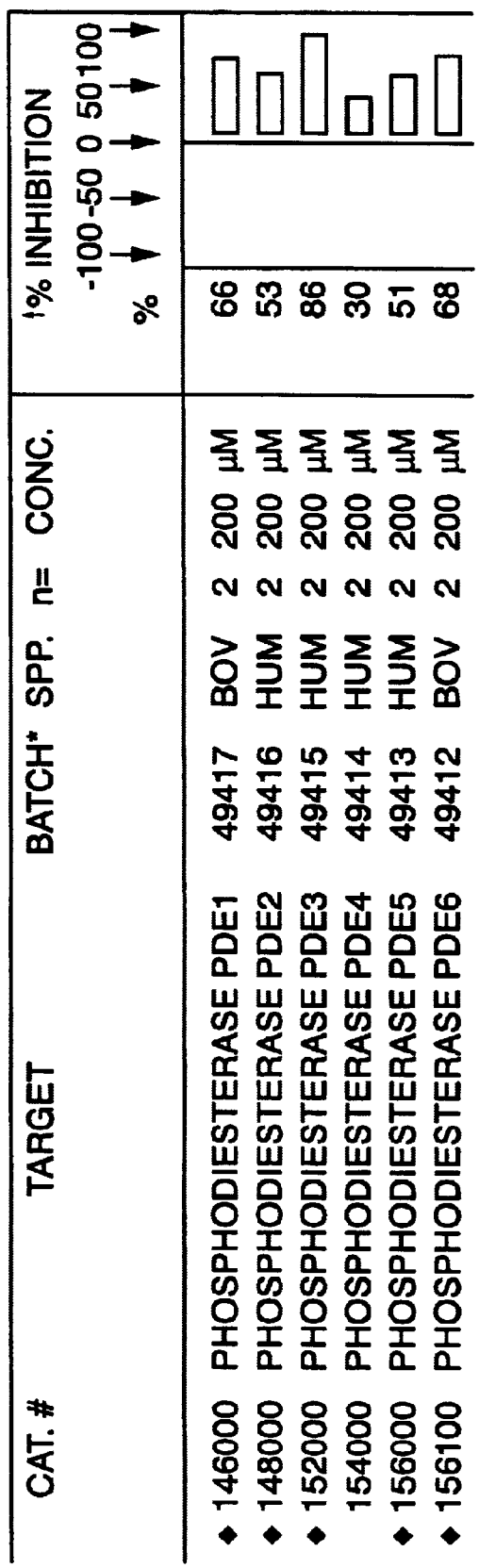
FIG. 20 depicts the results of in vitro phosphodiesterase inhibition assays using the (+)-enantiomer of monochloroflosequinan (i.e. (S)-(+)-3-chloromethyl sulfinyl-7-fluoro-1-methyl-4-quinolone).

FIG. 20 shows the results of assays carried out as described above with the (+)-enantiomer of monochloroflosequinan (i.e. (S)-(+)-3-chloromethylsulfinyl-7-fluoro-1-methyl-4-quinolone). Each PDE was assayed at 25° C. with 200 µM of the (+)-enantiomer of monochloroflosequinan (i.e. (S)-(+)-3-chloromethylsulfinyl-7-fluoro-1-methyl-4-quinolone). (in 1% DMSO as the vehicle). Significant inhibition (e.g. greater than 50% inhibition) of PDE1, PDE2, PDE3, PDE5, and PDE6 was observed in this assay.

All publications and patents mentioned in the above specification are herein incorporated by reference. Various modifications and variations of the described invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A composition comprising racemic 3-chloromethylsulfinyl-7-fluoro-1-methyl-4-quinolone.

2. A composition comprising (S)-(+)-3-chloromethylsulfinyl-7-fluoro-1-methyl-4-quinolone in enantiomeric excess.

3. A composition according to claim 2, wherein said (S)-(+)-3-chloromethylsulfinyl-7-fluoro-1-methyl-4-quinolone is at least 90% of the enantiomeric excess.

4. A composition according to claim 2, wherein said (S)-(+)-3-chloromethylsulfinyl-7-fluoro-1-methyl-4-quinolone is at least 95% of the enantiomeric excess.

5. A composition comprising (R)-(−)-3-chloromethylsulfinyl-7-fluoro-1-methyl-4-quinolone in enantiomeric excess.

6. A composition according to claim 5, wherein said (R)-(−)-3-chloromethylsulfinyl-7-fluoro-1-methyl-4-quinolone; is at least 90% of the enantiomeric excess.

7. A composition according to claim 5, wherein said (R)-(−)-3-chloromethylsulfinyl-7-fluoro-1-methyl-4-quinolone is at least 95% of the enantiomeric excess.

8. A composition comprising 3-chloromethylsulfonyl-7-fluoro-1-methyl-4-quinolone.

9. A composition comprising 3-chloromethylthio-7-fluoro-1-methyl-4-quinolone.

10. A method for the synthesis of chlorodesoxyflosequinan, comprising:

a) providing:
  i) flosequinan, and
  ii) triphenyl phosphine; and b) reacting said flosequinan and triphenyl phosphine in an organic solvent under conditions such that desoxyflosequinan (7-fluoro-1-methyl-3-methylthio-4-quinolone) is produced; and c) further reacting said desoxyflosequinan with N-chlorosuccinimide and 2,2'-azobisisobutyronitrile in an organic solvent under conditions such that chlorodesoxyflosequinan (3-chloromethylthio-7-fluoro-1-methyl-4-quinolone) is produced.

11. The method of claim 10, wherein said organic solvent in said reacting step b) is selected from the group consisting of carbon tetrachloride, xylene and toluene.

12. The method of claim 10, wherein said providing step a) optionally provides iii) a catalyst, and said reacting step b) occurs in the presence of said catalyst.

13. The method of claim 12, wherein said organic solvent in said reacting step b) is selected from the group consisting of xylene and toluene.

14. The method of claim 12, wherein said catalyst is tetrabromomethane.

15. The method of claim 10, wherein said organic solvent in step c) is selected from the group consisting of carbon tetrachloride and benzene.

16. A method for the synthesis of chlorodesoxyflosequinan, comprising:

a) providing:
  i) flosequinan,
  ii) thionyl chloride, and
  iii) pyridine; and b) reacting said flosequinan, thionyl chloride and pyridine in an organic solvent under conditions such that chlorodesoxyflosequinan (3-chloromethylthio-7-fluoro-1-methyl-4-quinolone) is produced.

17. A method for the synthesis of monochloroflosequinan, comprising:

a) providing:
  i) chlorodesoxyflosequinan (3-chloromethylthio-7-fluoro-1-methyl-4-quinolone),
  ii) hydrogen peroxide, and
  iii) potassium carbonate; and b) reacting said chlorodesoxyflosequinan, hydrogen peroxide and potassium carbonate in a solvent under conditions such that monochloroflosequinan (3-chloromethylsulfinyl-7-fluoro-1-methyl-4-quinolone) is produced.

18. A methods for the synthesis of monochloroflosequinan, comprising:

a) providing:
  i) flosequinan, and
  ii) N-chlorosuccinimide; and b) reacting said flosequinan and N-chlorosuccinimide in an organic solvent under conditions such that monochloroflosequinan (3-chloromethylsulfinyl-7-fluoro-1-methyl-4-quinolone) is produced.

19. The method of claim 18, wherein said organic solvent is selected from the group consisting of carbon tetrachloride and benzene.

20. The method of claim 19, wherein when said organic solvent is carbon tetrachloride, said reacting step b) additionally includes 2,2'-azobisisobutyronitrile.

21. A method for the synthesis of monochloroflosequinan, comprising:

a) providing:
   i) chlorodesoxyflosequinan (3-chloromethylthio-7-fluoro-1-methyl-4-quinolone), and
   ii) a camphor based reagent; and
b) reacting said chlorodesoxyflosequinan and camphor based reagent in an organic solvent under conditions such that an enantiomer of monochloroflosequinan is produced in enantiomeric excess.

22. The method of claim 21, wherein said camphor based reagent is (R)-(−)-(10-camphorsulfonyl) oxaziridine.

23. The method of claim 21, wherein said camphor based reagent is (S)-(+)-(10-camphorsulfonyl) oxaziridine.

24. The method of claim 22, wherein said enantiomer of monochloroflosequinan is (S)-(+)-3-chloromethylsulfinyl-7-fluoro-1-methyl-4-quinolone.

25. The method of claim 23, wherein said enantiomer of monochloroflosequinan is (R)-(−)-3-chloromethylsulfinyl-7-fluoro-1-methyl-4-quinolone.

26. A method for the synthesis of Monochloroflosequinan sulfone, comprising:
a) providing:
   i) monochloroflosequinan (3-chloromethylsulfinyl-7-fluoro-1-methyl-4-quinolone), and
   ii) m-chloroperoxybenzoic acid; and
b) reacting said monochloroflosequinan and m-chloroperoxybenzoic acid in an organic solvent under conditions such that monochloroflosequinan sulfone (3-chloromethylsulfonyl-7-fluoro-1-methyl-4-quinolone) is produced.

* * * * *